US012611341B2

(12) United States Patent
Wang et al.

(10) Patent No.: US 12,611,341 B2
(45) Date of Patent: Apr. 28, 2026

(54) ABSORBENT ARTICLES HAVING SPACER WOVEN FABRIC

(71) Applicant: The Procter & Gamble Company, Cincinnati, OH (US)

(72) Inventors: Sijia Wang, Beijing (CN); Fancheng Wang, Beijing (CN); Runze Qin, Beijing (CN); Wanning Li, Beijing (CH); Xiaoxin Liu, Beijing (CN); Meng Chen, Beijing (CN); Minxuan Xin, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 349 days.

(21) Appl. No.: 18/533,266

(22) Filed: Dec. 8, 2023

(65) Prior Publication Data

US 2024/0189163 A1      Jun. 13, 2024

(30) Foreign Application Priority Data

Dec. 9, 2022    (WO) ................ PCT/CN2022/137844

(51) Int. Cl.
A61F 13/539      (2006.01)
A61F 13/513      (2006.01)
A61F 13/56      (2006.01)

(52) U.S. Cl.
CPC .......... A61F 13/539 (2013.01); A61F 13/513 (2013.01); A61F 13/5605 (2013.01)

(58) Field of Classification Search
CPC ... A61F 13/539; A61F 13/513; A61F 13/5605
See application file for complete search history.

(56) References Cited

U.S. PATENT DOCUMENTS 5,554,243 A * 9/1996 Igaue .................... A61F 13/531
156/324
5,665,083 A * 9/1997 Igaue .................... A61F 13/531
428/137
(Continued)

FOREIGN PATENT DOCUMENTS

WO      WO-2005051656 A1 *  6/2005  ....... A61F 13/53743
WO        2014011927 A1    1/2014
(Continued)

OTHER PUBLICATIONS

PCT Search Report and Written Opinion for PCT/CN2022/137844 dated May 11, 2023, 13 pages.
(Continued)

*Primary Examiner* — Guy K Townsend
(74) *Attorney, Agent, or Firm* — Amanda Herman Berghauer

(57)      ABSTRACT

The present disclosure provides an absorbent article comprising a liquid permeable topsheet comprising a wearer facing surface and an opposite garment facing surface and a nonwoven, the nonwoven comprising a plurality of apertures, a liquid impermeable backsheet, an absorbent core disposed between the topsheet and the backsheet; and a fluid management layer disposed between the topsheet and the absorbent core, the fluid management layer comprising a spacer woven fabric, wherein the nonwoven comprises a first surface forming the wearer facing surface of the topsheet, and a second surface forming the garment facing surface of the topsheet, the first surface having a first contact angle of no lower than about 90 degrees, and wherein the spacer woven fabric comprises a top face, a bottom face, and a plurality of yarns interconnecting the first and second faces, wherein the first and second faces are spaced apart from each other.

16 Claims, 14 Drawing Sheets

(56) References Cited

U.S. PATENT DOCUMENTS

| | | | | |
|---|---|---|---|---|
| 6,245,051 | B1 * | 6/2001 | Zenker | A61F 13/5376 |
| | | | | 604/385.23 |
| 6,437,214 | B1 * | 8/2002 | Everett | A61F 13/5376 |
| | | | | 604/378 |
| 6,673,982 | B1 * | 1/2004 | Chen | A61F 13/53743 |
| | | | | 604/385.101 |
| 6,802,834 | B2 * | 10/2004 | Melius | A61F 13/535 |
| | | | | 604/378 |
| 7,745,687 | B2 * | 6/2010 | Heyn | A61F 13/15626 |
| | | | | 604/378 |
| 8,206,533 | B2 * | 6/2012 | Hundorf | B32B 5/30 |
| | | | | 156/305 |
| 8,216,666 | B2 * | 7/2012 | Warner | A61F 13/51496 |
| | | | | 428/323 |
| 8,658,852 | B2 * | 2/2014 | Paldey | A61F 13/539 |
| | | | | 604/379 |
| 8,748,693 | B2 * | 6/2014 | Westwood | B32B 5/028 |
| | | | | 604/383 |
| 8,936,586 | B2 * | 1/2015 | Roe | A61F 13/4906 |
| | | | | 604/385.15 |
| 9,078,792 | B2 * | 7/2015 | Ruiz | A61F 13/74 |
| 11,033,440 | B2 * | 6/2021 | Isele | A61F 13/551 |
| 11,273,083 | B2 * | 3/2022 | Bewick-Sonntag | |
| | | | | A61F 13/15699 |
| 11,285,056 | B2 * | 3/2022 | Erdem | B32B 7/09 |
| 11,779,496 | B2 * | 10/2023 | Lindner | B01J 20/264 |
| | | | | 604/368 |
| 11,878,492 | B2 * | 1/2024 | Lindner | B32B 5/022 |
| 12,357,515 | B2 * | 7/2025 | Van Malderen | A61F 13/5323 |
| 12,404,434 | B2 * | 9/2025 | Turner | C08L 23/26 |
| 2003/0114520 | A1 * | 6/2003 | Pereira | A61K 8/86 |
| | | | | 514/532 |
| 2007/0043330 | A1 * | 2/2007 | Lankhof | A61F 13/51394 |
| | | | | 604/378 |
| 2009/0137975 | A1 * | 5/2009 | Kohira | D04H 3/11 |
| | | | | 604/385.01 |
| 2010/0249738 | A1 * | 9/2010 | Tondkar | A61F 13/49 |
| | | | | 604/367 |
| 2011/0118686 | A1 * | 5/2011 | Vega | A61F 13/8405 |
| | | | | 560/190 |
| 2013/0046263 | A1 * | 2/2013 | Fukudome | B32B 5/022 |
| | | | | 604/375 |
| 2014/0005622 | A1 * | 1/2014 | Wirtz | A61F 13/539 |
| | | | | 604/366 |
| 2014/0005623 | A1 * | 1/2014 | Wirtz | A61F 13/53418 |
| | | | | 604/366 |
| 2014/0163500 | A1 * | 6/2014 | Roe | A61F 13/49001 |
| | | | | 604/374 |
| 2014/0163501 | A1 * | 6/2014 | Ehrnsperger | A61F 13/49 |
| | | | | 604/374 |
| 2014/0163506 | A1 * | 6/2014 | Roe | A61F 13/535 |
| | | | | 604/378 |
| 2014/0163511 | A1 * | 6/2014 | Roe | A61F 13/532 |
| | | | | 604/385.101 |
| 2014/0303582 | A1 * | 10/2014 | Wright | A61F 13/15658 |
| | | | | 156/60 |
| 2014/0329943 | A1 * | 11/2014 | Jakupca | C08L 85/02 |
| | | | | 558/156 |
| 2014/0378590 | A1 * | 12/2014 | Jakupca | C08G 65/3353 |
| | | | | 558/87 |
| 2015/0005727 | A1 * | 1/2015 | Matsushita | A61L 15/26 |
| | | | | 442/382 |
| 2015/0065976 | A1 * | 3/2015 | Roe | A61F 13/42 |
| | | | | 604/374 |
| 2015/0080821 | A1 * | 3/2015 | Peri | C08J 3/245 |
| | | | | 604/385.01 |
| 2015/0148764 | A1 | 5/2015 | Latimer | |
| 2015/0203636 | A1 * | 7/2015 | Jakupca | C08L 23/12 |
| | | | | 558/87 |
| 2016/0002384 | A1 * | 1/2016 | Nacharaju | A61Q 5/06 |
| | | | | 525/132 |
| 2016/0136014 | A1 * | 5/2016 | Arora | B32B 5/022 |
| 2016/0243259 | A1 * | 8/2016 | Almarsson | A61K 38/00 |
| 2016/0270982 | A1 * | 9/2016 | Raycheck | A61F 13/55105 |
| 2016/0354260 | A1 * | 12/2016 | Roe | A61F 13/532 |
| 2016/0376263 | A1 * | 12/2016 | Patron | A61K 8/4973 |
| | | | | 514/784 |
| 2017/0087199 | A1 * | 3/2017 | Patron | A61K 31/381 |
| 2017/0096418 | A1 * | 4/2017 | Patron | A23L 33/10 |
| 2017/0156947 | A1 * | 6/2017 | Esquerra | A61F 13/496 |
| 2017/0157021 | A1 * | 6/2017 | Traynor | A61K 8/466 |
| 2017/0216164 | A1 * | 8/2017 | Traynor | A61K 8/895 |
| 2017/0216165 | A1 * | 8/2017 | Traynor | A01N 25/28 |
| 2017/0258651 | A1 | 9/2017 | Hammons | |
| 2017/0281425 | A1 * | 10/2017 | Herfert | A61F 13/535 |
| 2017/0312149 | A1 * | 11/2017 | Bianchi | A61F 13/537 |
| 2019/0015304 | A1 * | 1/2019 | Musa | A61K 8/06 |
| 2019/0133835 | A1 * | 5/2019 | Bewick-Sonntag | |
| | | | | A61F 13/15731 |
| 2019/0192354 | A1 * | 6/2019 | Bewick-Sonntag | A61F 13/47 |
| 2019/0240083 | A1 | 8/2019 | Bernhuber | |
| 2019/0240084 | A1 * | 8/2019 | Rosati | A61F 13/513 |
| 2019/0290940 | A1 * | 9/2019 | Traynor | A61Q 19/00 |
| 2019/0375875 | A1 * | 12/2019 | Musa | A61K 8/817 |
| 2019/0382519 | A1 * | 12/2019 | Musa | A61K 8/06 |
| 2020/0000693 | A1 * | 1/2020 | Traynor | A61K 47/02 |
| 2020/0108168 | A1 * | 4/2020 | Turner | D04H 1/5405 |
| 2021/0169709 | A1 * | 6/2021 | Bauer | A61L 15/24 |
| 2021/0251823 | A1 * | 8/2021 | Yuan | A61F 13/15203 |
| 2022/0287944 | A1 * | 9/2022 | Costache | A61K 8/64 |
| 2022/0323269 | A1 * | 10/2022 | Burn Lees | A61L 15/28 |
| 2022/0409448 | A1 | 12/2022 | Okada | |
| 2024/0189163 | A1 * | 6/2024 | Wang | A61F 13/5605 |

FOREIGN PATENT DOCUMENTS

| | | | | |
|---|---|---|---|---|
| WO | | 2017158487 A1 | 9/2017 | |
| WO | | WO-2020210995 A1 * | 10/2020 | D04H 1/593 |

OTHER PUBLICATIONS

All Office Actions; U.S. Appl. No. 18/533,263, filed on Dec. 8, 2023.

All Office Actions; U.S. Appl. No. 18/533,270, filed on Dec. 8, 2023.

Unpublished U.S. Appl. No. 18/533,263, filed on Dec. 8, 2023, to Xiaoxin Liu et al.

Unpublished U.S. Appl. No. 18/533,270, filed on Dec. 8, 2023, to Tong Tong et al.

* cited by examiner 1 mm 1 mm

ABSORBENT ARTICLES HAVING SPACER WOVEN FABRIC

CROSS REFERENCE TO RELATED APPLICATION

This application claims foreign priority under 35 U.S.C. § 119 to Chinese Patent Application No. PCT/CN2022/137844, filed on Dec. 9, 2022, which is herein incorporated by reference in its entirety.

FIELD OF THE INVENTION

The present invention relates to an absorbent article comprising a fluid management layer comprising a spacer woven fabric.

BACKGROUND OF THE INVENTION

Absorbent articles for personal hygiene, such as sanitary napkins, adult incontinence undergarments, disposable diapers for infants, and/or training pants for toddlers are designed to absorb and contain bodily exudates, in particular large quantities of menses, urine, and/or runny BM (together the "fluids").

Users of such disposable absorbent articles have several concerns. Leakage from products like catamenial pads, diapers, sanitary napkins, and incontinence pads is a significant concern. To prevent fluid leakage, absorbent articles are desired to provide a high acquisition speed. Wetness feel is also a concern to be considered, so that rewet due to fluid-back to a topsheet from other components of the absorbent article need to be effectively mitigated or prevented. It is also a desirable characteristic of an absorbent article to present a clean user contacting surface with less stain.

These absorbent articles are generally designed to comprise several layers providing different functions. A liquid permeable topsheet is disposed closest to the wearer's skin and should be capable of quickly absorbing the excreted fluid. A backsheet is disposed on the opposed, garment-facing side of the article. Absorbent cores comprising various absorbent materials are desired to absorb body fluid from a topsheet quickly and have high fluid storage capacity.

It has been known that hydrophilic topsheets exhibit faster acquisition speed compared to hydrophobic topsheet; however, it tends to cause wetness sensation as it traps or retains the fluid, and/or the fluid is flow-back through a topsheet due to high affiliation of constituting fibers to the fluid. Absorbent articles having hydrophobic topsheets may be preferred by some consumers because they provide dryness feel and good blurring/masking benefits regarding menses/urine staining. However, hydrophobic topsheets absorb the fluid only via capillary force which can lead to slower acquisition speed and causes fluid leakage problems.

Absorbent cores commonly used in absorbent articles comprise various absorbent materials. To meet the need for a thin absorbent article, an absorbent core often includes a high amount of superabsorbent polymers. Superabsorbent polymers have a high absorption capacity but a relatively slow absorption speed, so that absorbent articles with an absorbent core comprising high amount of superabsorbent polymers often may not be able to absorb instantaneously a large amount of fluid discharged during a few seconds.

Absorbent articles commonly employ a fluid management layer between a topsheet and an absorbent core which can quickly receive large amounts of fluid from a topsheet and temporarily store it before the fluid is absorbed by the absorbent core. Therefore, one desirable function of a fluid management layer is to quickly acquire fluid from a topsheet and transfer it to the absorbent core in an efficient manner. Another one is to reduce fluid amount in the topsheet to avoid a wetness sensory.

To quickly remove the fluid in a topsheet, one approach is to develop a fluid management layer having a good wicking property to distribute the fluid along a planar direction of the fluid management layer to lower the fluid concentration at the loading point, and a high capillary force to suck down the fluid from the topsheet. Both a wicking property and a capillary force may be contributed by small pore sizes either in a planar direction or a z-direction. While small size pores in a fluid management layer enhances a wicking property and a capillary force, it also brings a high flow resistance of the fluid to penetrate the fluid management layer which results in slowing acquisition speed. Therefore, there is typically a tradeoff between acquisition speed and wet sensory (or rewet).

WO2005/051657A discloses a multi-layer fluid management fabric composite comprising a three-dimensional fabric spacer forming a first layer of the fabric composite, a plurality of overlying moisture-absorbent cores residing outside of the spacer, and a liquid impermeable jacket residing outside of the absorbent cores. The three-dimensional fabric spacer in WO2005/051657A comprises a first facing, an opposite second facing, and an intermediate spacer yarn interconnecting the first and second facings. WO2014/1011927 discloses an absorbent article comprising a fluid flow control member which is a spacer woven fabric located between a topsheet and an absorbent core wherein the spacer woven fabric comprises a top layer, a bottom layer and an interconnecting layer of yarns between the top layer and the bottom layer.

As such there is a need for an absorbent article which can provide a rapid fluid acquisition speed without compromising a dry sensory feel or a low rewet.

There is also a continuous need for an absorbent article which can provide improved surface cleanness against body fluid without compromising fluid handling properties such as a rapid fluid acquisition speed and mitigated rewet.

SUMMARY OF THE INVENTION

The present invention provides an absorbent article comprising a liquid permeable topsheet having a wearer facing surface and an opposite garment facing surface, wherein the topsheet comprises a nonwoven comprising a plurality of apertures, a liquid impermeable backsheet, an absorbent core disposed between the topsheet and the backsheet, and a fluid management layer disposed between the topsheet and the absorbent core, the fluid management layer comprising a spacer woven fabric. The nonwoven comprises a first surface forming the wearer facing surface of the topsheet, and a second surface forming the garment facing surface of the topsheet, the first surface having a first contact angle of no lower than about 90 degrees as measured according to Contact Angle Test, and wherein the spacer woven fabric comprises a top face, a bottom face, and a plurality of yarns interconnecting the first and second faces, wherein the first and second faces are spaced apart from each other.

Due to a unique combination of a topsheet comprising a hydrophobic nonwoven forming a wear-facing surface and a fluid management layer comprising a spacer woven fabric, the absorbent article of the present invention can provide a fast liquid acquisition speed and clean surface without compromising dry sensory feel.

These and other features, aspects, and advantages of the present invention will become evident to those skilled in the art from a reading of the present disclosure.

DETAILED DESCRIPTION OF THE INVENTION

Figure 1:
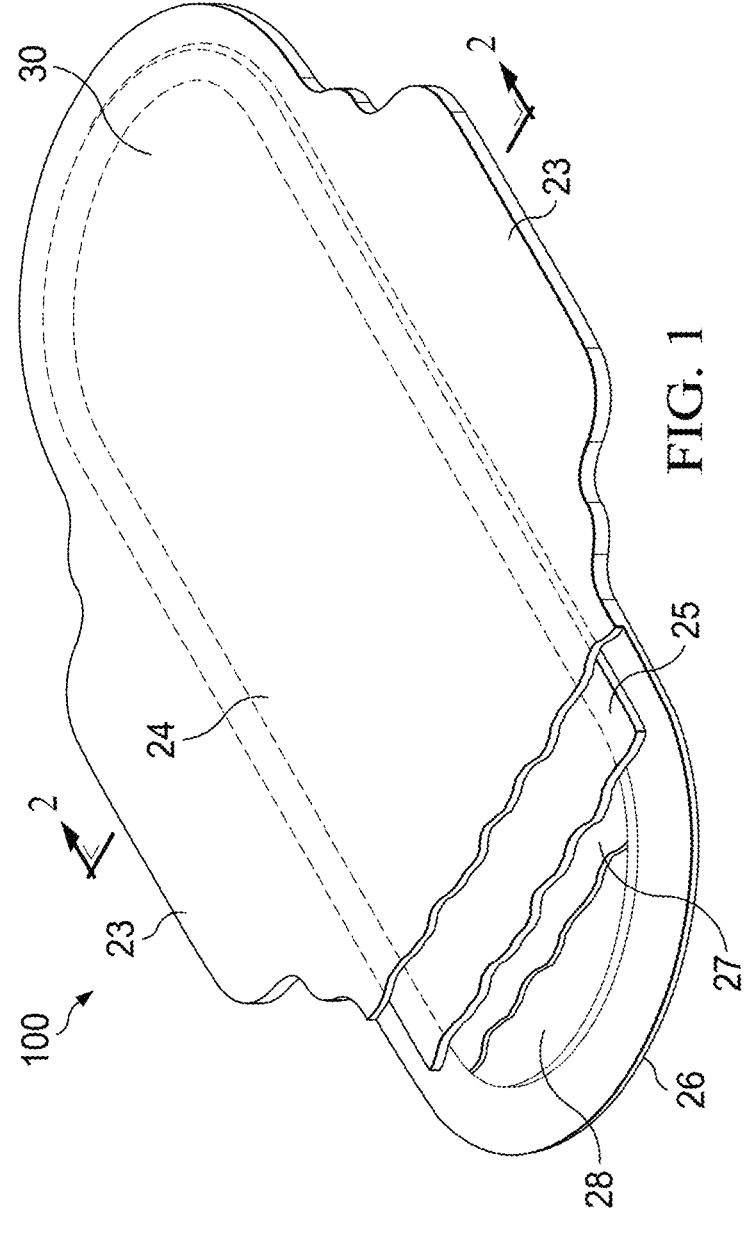
FIG. 1 is a perspective view of an exemplary absorbent article.

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent articles", as used herein, include disposable diapers, sanitary napkins, panty liners, incontinence pads, interlabial pads, breast-milk pads, sweat sheets, animal-use excreta handling articles, animal-use diapers, and the like.

The term "joined", as used herein, refers to the condition where a first member is attached, or connected, to a second member either directly or indirectly. Where the first member is attached, or connected, to an intermediate member which in turn is attached, or connected, to the second member, the first member and second member are joined indirectly.

The term "integrated" as used herein is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needle punching. Spunlacing uses a plurality of high pressure water jets to entangle fibers.

The term "carded" as used herein is used to describe structural features of the fluid management layers described herein. A carded nonwoven utilizes fibers which are cut to a specific length, otherwise known as "staple length fibers." Staple length fibers may be any suitable length. For example, staple length fibers may have a length of up to 120 mm or may have a length as short as 10 mm. However, if a particular group of fibers are staple length fibers, for example viscose fibers, then the length of each of the viscose fibers in the carded nonwoven is predominantly the same, i.e. the staple length. It is worth noting that where additional staple fiber length fiber types are included, for example, polypropylene fibers, the length of each of the polypropylene fibers in the carded nonwoven is also predominantly the same. But the staple length of the viscose and the staple length of the polypropylene may be different.

In contrast, continuous filaments such as by spunbonding or meltblowing processes, do not create staple length fibers. Instead, these filaments are of an indeterminate length and are not cut to a specific length as noted regarding their staple fiber length counterparts.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e., in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e., orthogonal to the length of the article or component thereof, and typically it refers to the distance/size of the dimension parallel of the transverse axis of the article or component.

As used herein, the terms "hydrophilic" and "hydrophobic" have meanings that are well established in the art with respect to the contact angle of water on the surface of a material. Thus, a material having a water contact angle of greater than about 90° as measured by Contact Angle Test is considered hydrophobic, and a material having a water contact angle of less than about 90° as measured by Contact Angle Test is considered hydrophilic.

Absorbent Article

Figure 2:
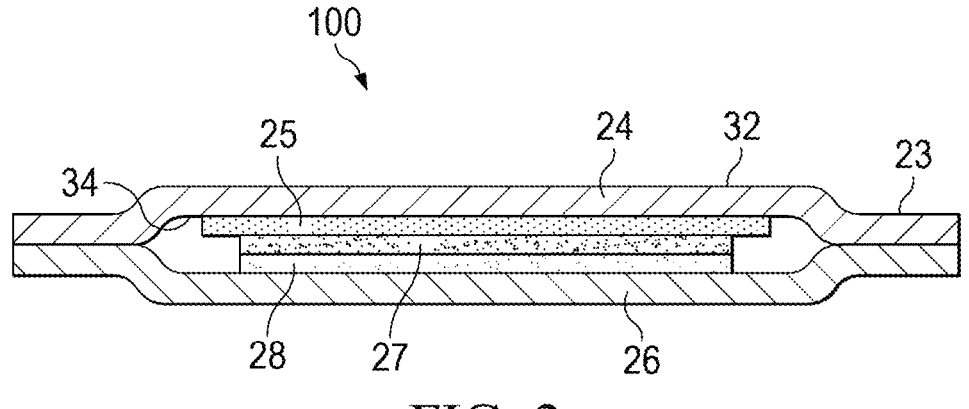
FIG. 2 is a lateral cross-section view along 2-2 of the absorbent article of FIG. 1.

Absorbent articles will now be generally discussed and further illustrated in the form of a sanitary napkin 100 as exemplarily represented in FIGS. 1 and 2. FIG. 1 is a plan view of the exemplary sanitary napkin 100 in a flattened-out configuration and the wearer facing side turned up. FIG. 2 is a lateral cross-section view along 2-2 of the absorbent article of FIG. 1.

Referring to FIGS. 1 and 2, an absorbent article according to the present disclosure, a sanitary napkin 100 for example, comprises a topsheet 24 having a wearer facing surface and a garment facing surface positioned opposite to the wearer facing surface. The topsheet 24 comprises nonwoven 30 where a top surface 32 of the nonwoven 30 forms the wearer facing surface of the topsheet 24.

The absorbent article further comprises a backsheet 26 having a garment facing surface and a wearer facing surface positioned oppositely to the garment facing surface, the backsheet 26 being at least partially joined to the topsheet 24. The absorbent article also comprises an absorbent core 28 positioned between the topsheet 24 and the backsheet 26. The absorbent article further comprises a fluid management layer 27 positioned between the topsheet 24 and the absorbent core 28. The absorbent article may further comprise additional fluid acquisition and/or distribution layer 25 (or system). The absorbent article may further comprise a pair of flaps or wings 23. The topsheet 24, the backsheet 26, the fluid management layer 27, and the absorbent core 28, and other optional elements can be assembled in a variety of well-known configurations.

The backsheet 26 and the topsheet 24 can be secured together in a variety of ways. The topsheet 24 and the backsheet 26 can be joined to each other by using an adhesive, heat bonding, pressure bonding, ultrasonic bonding, dynamic mechanical bonding, or a crimp seal. A fluid impermeable crimp seal can resist lateral migration ("wicking") of fluid through the edges of the product, inhibiting side soiling of the user's undergarments.

When the absorbent article is a sanitary napkin as shown in FIG. 1, as is typical for sanitary napkins and the like, the sanitary napkin can have panty-fastening adhesive disposed on the garment facing side of backsheet 26. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the user's panties.

Topsheet

A topsheet is generally liquid permeable and is configured to receive fluids being excreted from the body and aid in directing the fluids toward a fluid management layer and/or the absorbent core. One particularly desirable quality of a topsheet is the ability to reduce ponding of the fluids on the topsheet before the fluids are able to be absorbed by the absorbent article. Another particularly desirable quality of a topsheet is to reduce rewet of the topsheet. It may also be desirable that the topsheet presents a clean user contacting surface with relatively less stain.

The topsheet of the present disclosure is part of an absorbent article that is in contact with the wearer's skin during use of the article. The topsheet may be joined to portions of the backsheet, the absorbent core, and/or any other layers as is known to those of ordinary skill in the art. Further, at least a portion of, or all of, the topsheet may be liquid permeable, permitting the body fluid to readily penetrate through its thickness.

The topsheet described herein has a wearer facing surface forming the wearer facing surface of the absorbent article and an opposite garment facing surface, and may comprise a nonwoven comprising a plurality of apertures.

In some configurations, the nonwoven constituting the topsheet comprises a first surface forming the wearer facing surface of the topsheet, and a second surface forming the garment facing surface of the topsheet. The first surface of the nonwoven has a first contact angle of no lower than about 90 degrees, or no lower than 95 degrees, or no lower than 100 degrees as measured according to Contact Angle Test. The second surface of the nonwoven may have a second contact angle of no lower than about 90 degrees as measured according to Contact Angle Test. The second surface of the nonwoven may have a second contact angle of lower than about 90 degrees as measured according to Contact Angle Test. In some configurations, the difference between the first contact angle and the second angle is at least about 10 degrees, or at least about 15 degrees, or at least about 20 degrees, as measured according to Contact Angle Test. The nonwoven with a second surface having a second contact angle of lower than about 90 degrees may provide a faster acquisition speed compared to a nonwoven with a second surface having a second contact angle of no lower than about 90 degrees.

The nonwoven comprises a first layer comprising hydrophobic fibers. The nonwoven may further comprise a second layer comprising hydrophilic fibers. When the nonwoven forms a topsheet of an absorbent article according to the present disclosure, the first layer forms a wearer facing surface of the topsheet. When the nonwoven comprises the first layer and the optional second layer, the first layer forms a wearer facing surface of the topsheet and the second layer forms the garment facing surface of the topsheet.

When the nonwoven forming a topsheet of an absorbent article according to the present disclosure comprises two or more layers, the two or more layers may form a unitary structure or may remain as discrete layers. A unitary structure herein intends to mean that although it may be formed by several sub-layers or stratums that have distinct properties and/or compositions from one another, they are somehow intermixed at the boundary region so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition. Or each of sub-layer is produced in a separate step and the sub-layers are combined together in a face to face relationship. The sub-layers can be integrated via a known integration or bonding process such as spunlacing processes, hydroentangling, calendar bonding, through-air bonding and resin bonding.

Typically, there is no adhesive used between the sub-layers of the unitary material. However, in some cases, adhesives and/or binders can be present although typically in a lower amount.

When the topsheet of the present disclosure is described herein, terms of layer(s), sub-layer(s), and stratum (strata) are interchangeable. Relating to descriptions of a topsheet with unitary structure, the terms of layer(s) and stratum(s) are interchangeable.

When the topsheet in the present disclosure comprises two or more layers which remain as discrete layers, the two or more layers may be attached at least partially to each other by, for example, thermal bonding, adhesive bonding, ultrasonic bonding, or any combination thereof.

The topsheet in the present disclosure may have various structures.

Figure 3A:
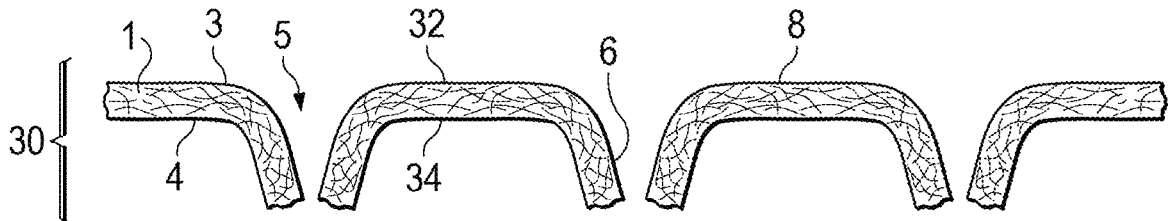
FIG. 3A is a schematic view of nonwoven constituting a topsheet of an absorbent article.
Figure 3B:
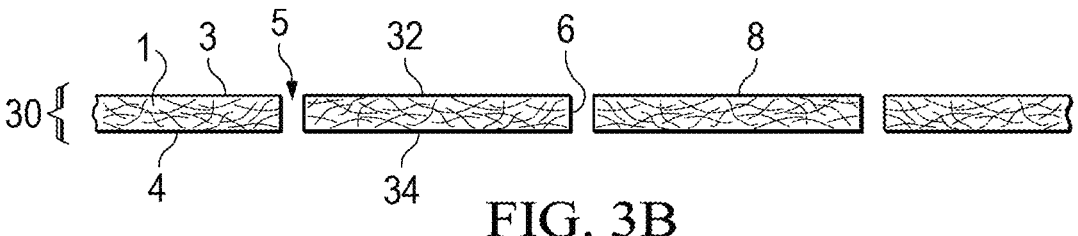
FIG. 3B is a schematic view of nonwoven constituting a topsheet of an absorbent article.

Referring to FIGS. 3A and 3B, nonwoven 30 constituting a topsheet disclosed herein comprises at least a first layer 1. The first layer 1 comprises a first surface 3 which forms a wearer facing surface of the topsheet, and an opposite second surface 4.

Figures 4, 5:
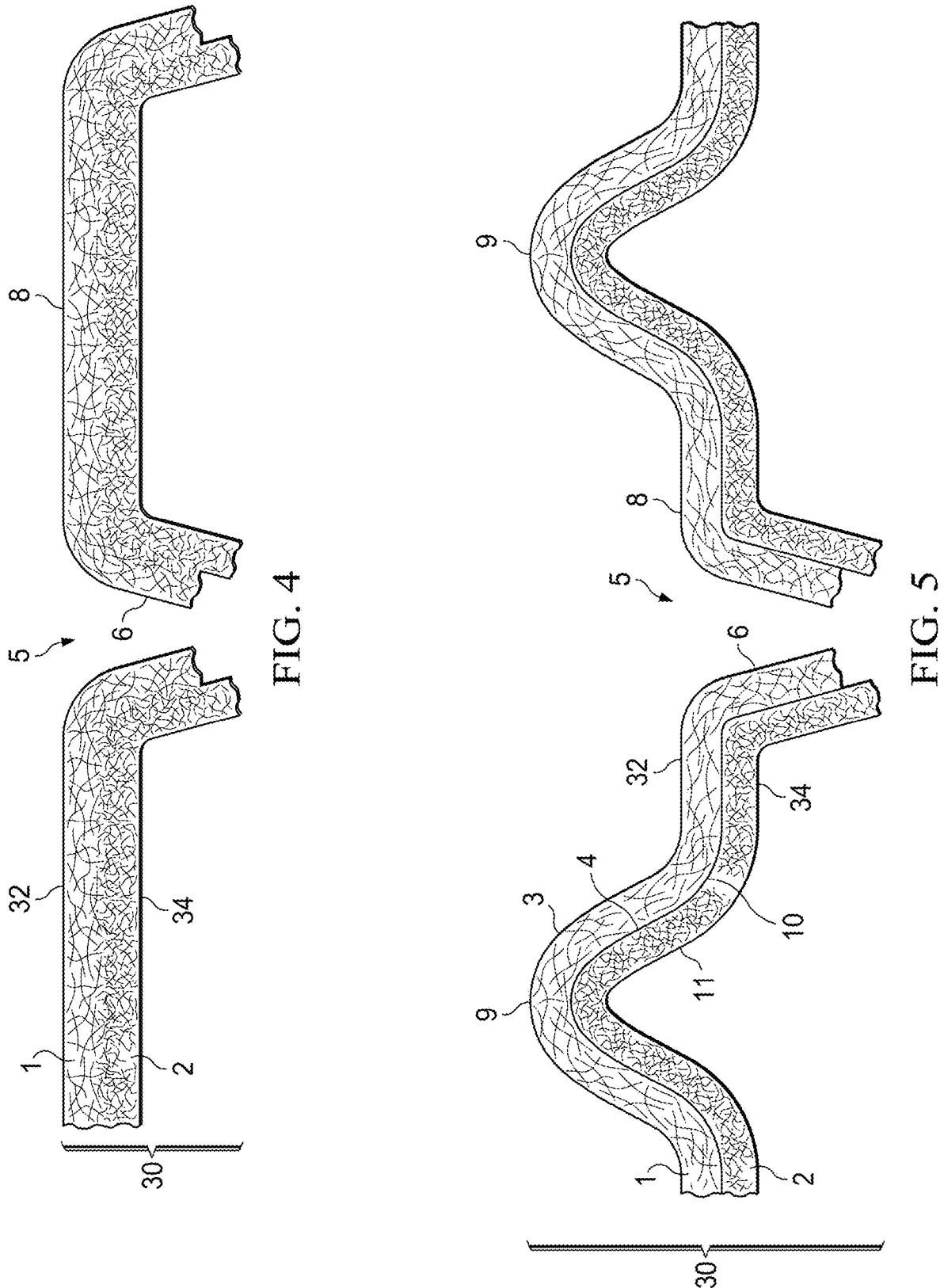
FIG. 4 is a schematic view of nonwoven constituting a topsheet of an absorbent article.
FIG. 5 is a schematic view of nonwoven constituting a topsheet of an absorbent article.

Referring to FIGS. 4 and 5, nonwoven 30 constituting a topsheet disclosed herein may comprise a first layer 1 forming a wearer facing surface of a topsheet, and a second layer 2 forming a garment facing surface of the topsheet.

Referring to FIG. 4, nonwoven 30 may have unitary structure, and the first layer 1 and the second layer 2 are intermixed at the boundary region instead of having a definite boundary between the two layers.

Referring to FIG. 5, nonwoven 30 may be a laminate of separate layers, a first layer 1 and a second layer 2 in this case, which are joined to each other in a face to face relationship. The first layer 1 has a first surface 3 forming a wearer facing surface of a topsheet, and a second surface 4. The second layer has a first surface 10, and a second surface 11 forming a garment facing surface of the topsheet. Still referring to FIG. 5, the topsheet 24 may comprise a plurality of protrusions 9. The nonwoven 30 may comprises land area 8 between the majority of the apertures 5. The land area may be substantially flat. The majority of the protrusions 9 may protrude outwardly from the land area 8 of the nonwoven 30.

The plurality of the protrusions 9 may be uniformly distributed on a wearer facing surface of a topsheet. The plurality of the protrusions 9 may be unevenly distributed and form a shape or a pattern on the wearer facing surface of the topsheet. The majority of the protrusions 9 may be surrounded by at least one land area 8 and/or a plurality of apertures 5. The land area 8, the aperture 5 and the protrusion 9 may form a three-dimensional surface on the wearer facing surface of the topsheet.

In some configurations, the majority of the protrusions 9 may be hollow. When the topsheet comprises the first layer 1 and the second layer 2, viewing from the first surface 3 of the first layer 1, the protrusions 9 are protrude from the land area 8 of the first layer 1 in the same direction, and the first layer 1 and the second layer 2 are spaced apart from each other. The hollow between the first layer and the second layer can improve breathability of the topsheet.

Figure 6:
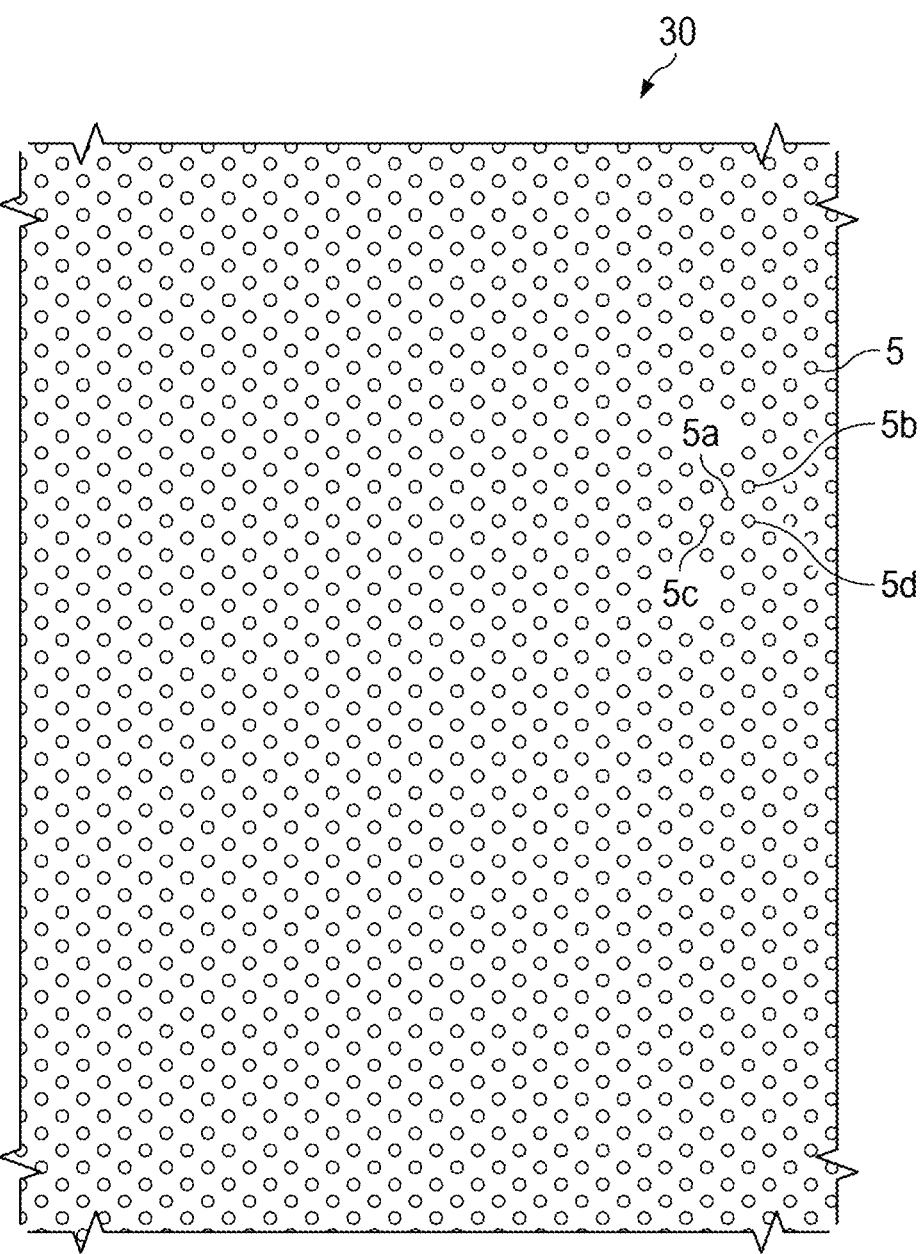
FIG. 6 is a top schematic view of an exemplary topsheet of an absorbent article of the invention.
Figure 7:
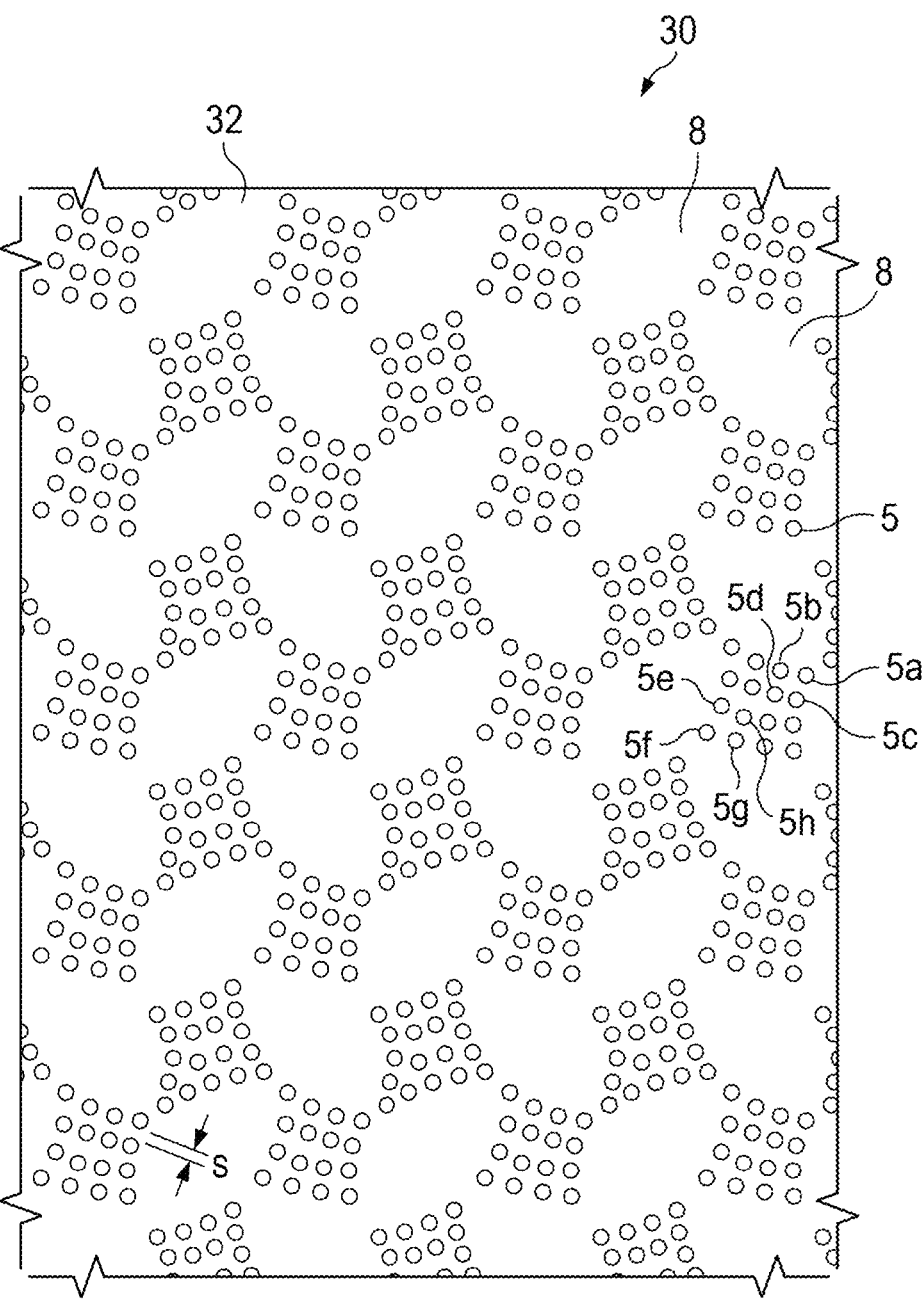
FIG. 7 is a top schematic view of another exemplary topsheet of an absorbent article of the invention.

The nonwoven may comprise a plurality of apertures 5. The nonwoven 30 may comprise at least one non-aperture area which has substantially no aperture. The non-aperture area may be a flat land area 8 and/or a protrusion 9. Referring to FIGS. 6 and 7, the nonwoven 30 constituting topsheet 24 may comprise at least one non-aperture area, land area 8 in this case, which has no aperture. The non-aperture area may fully surround the apertures. The non-aperture area may together form a generally continuous grid throughout the wearer facing surface of the topsheet, while the apertures may be discrete elements dispersed in and surrounded by the continuous grid.

Referring to FIG. 7, the non-aperture area may be a plurality of discrete areas defined by apertures. Each of the plurality of discrete non-aperture areas has a periphery formed by a continuous line of apertures.

When the topsheet described herein is incorporated into an absorbent article, the optional plurality of protrusions may protrude toward the skin of the wearer when the article is in use and away from the absorbent core of the absorbent article.

This three-dimensional first layer of the nonwoven provides better softness to the topsheet. It also helps maintain the skin of the wearer away from body fluids in the land area as the protrusions essentially create a space between the skin of the wearer and the body fluids.

The nonwoven constituting the topsheet in the present disclosure may have a basis weight from about 20 to about 100 g/m², or from about 30 to about 60 g/m², or about 20 to about 50 g/m², or about 30 to about 50 g/m².

First Layer

The first layer of the nonwoven comprises hydrophobic thermoplastic fibers. In some configurations, 100% of constituting fibers of the first layer are hydrophobic fibers.

Thermoplastic fibers may be selected from the group consisting of polyesters, polypropylenes, polyethylenes, polyethers, polyamides, polyhydroxyalkanoates, polysaccharides, and combinations thereof. Additionally, other synthetic fibers such as rayon, polyethylene, and polypropylene fibers can be used within the scope of the present disclosure.

Thermoplastic fibers may be single component fibers (i.e., single synthetic material or a mixture to make up the entire fiber), multicomponent fibers, such as bicomponent fibers (i.e., the fiber is divided into regions, the regions including two or more different synthetic materials or mixtures thereof), and combinations thereof.

The first layer may comprise semi-synthetic fibers made from polymers, specifically hydroxyl polymers. The topsheet may also comprise semi-synthetic fibers made from polymers, specifically hydroxyl polymers. Non-limiting examples of suitable hydroxyl polymers include polyvinyl alcohol, starch, starch derivatives, chitosan, chitosan derivatives, cellulose derivatives such as viscose, gums, arabinans, galactans, Lyocell (Tencel®), and combinations thereof.

The first layer may also comprise cellulose-based fibers which may be selected from the group consisting of wheat straw fibers, rice straw fibers, flax fibers, bamboo fibers, cotton fibers, jute fibers, hemp fibers, sisal fibers, bagasse fibers, hesperaloe fibers, and combinations thereof.

Several examples of the first layer may include, but are not limited to: spunbonded nonwovens; carded nonwovens; carded air through nonwovens; spunlace nonwovens, needle punched nonwovens and nonwovens with relatively specific properties to be able to be readily deformed.

The first layer can be formed from many processes, such as, for example, air laying processes, wetlaid processes, meltblowing processes, spunbonding processes, needle punching processes and carding processes.

Hydrophilic fibers may be rendered hydrophobic by treatment with a hydrophobic treatment such as a hydrophobic surfactant, e.g., by spraying or kiss roll coating hydrophilic fibers with a hydrophobic treatment, by dipping fibers into a hydrophobic treatment or by including a hydrophobic treatment as part of the polymer melt in producing thermoplastic fibers. Upon melting and resolidification, the treatment will tend to remain at the surfaces of the fiber.

The first layer may be a carded nonwoven.

Hydrophobic fibers constituting the first layer 1 has a contact angle higher than about 90 degrees, or higher than about 100 degrees. Constituent fibers of the first layer 1 may have a contact angle no greater than 150 degrees, or no greater than 130 degrees. The hydrophobicity of the constituent fibers can be adjusted by appropriately adjusting the degree of hydrophobilization treatment of the thermoplastic fibers, for example, the type and content of the hydrophobic treatment.

Hydrophobic fibers constituting the first layer may have a fiber fineness no greater than 4 denier, or 2.5 denier, or no greater than 2 denier, or no greater than 1.5 denier.

The first layer may have a basis weight from about 5 g/m² to about 30 g/m², or from about 8 g/m² to about 30 g/m², or about 8 g/m² to about 17 g/m², or about 8 g/m² to about 14 g/m².

Second Layer:

The nonwoven constituting the topsheet disclosed herein may comprises a second layer comprising hydrophilic fibers.

Constituting fibers of the second layer may be natural fibers, synthetic fibers or a combination of natural and synthetic fibers. In one embodiment, the second layer comprises thermoplastic fibers.

The list of synthetic fibers corresponds to the list disclosed above for the topsheet and the first layer.

Hydrophobic fibers may be rendered hydrophilic by treatment with a hydrophilic treatment such as a hydrophilic surfactant, e.g., by spraying hydrophobic thermoplastic with a hydrophilic treatment, by dipping the fiber into a treatment or by including a hydrophilic treatment as part of the polymer melt in producing thermoplastic fibers. Upon melting and resolidification, the treatment will tend to remain at the surfaces of the fiber.

Hydrophilic fibers constituting the second layer may have a fiber fineness no greater than 4 denier, or 2.5 denier, or no greater than 2 denier, or no greater than 1.5 denier.

The second layer may have a basis weight from about 10 $g/m^2$ to about 70 $g/m^2$, or from about 15 $g/m^2$ to about 60 $g/m^2$, or about 10 $g/m^2$ to about 40 $g/m^2$.

The first layer and/or the second layer web may be made by carded webs such as parallel webs, semi-random webs, random webs, cross-webs, criss-cross webs, and the like, air-laid webs, wet-laid webs, and spunbond webs, and the like. The first and the second fibrous webs may be the same, or different.

The thermal treatment of each web or a complex fibrous web can be conducted using any conventionally known thermal treatment method. Examples of preferable treating process include a thermal treatment apparatus such as a hot air through-type thermal treatment apparatus, a hot air blowing thermal treatment apparatus, an infrared thermal treatment apparatus, or the like. These thermal treatment apparatuses are typically provided with a conveying support for supporting and conveying a fibrous web. Thermal treatment may be performed under conditions such that the sheath components of the first and the second core/sheath composite fibers sufficiently melt and/or soften, and bond at a point of contact or intersection of the fibers, and such that crimps of the first and the second core/sheath composite fiber does not collapse.

All aspects described above for the first layer, except for the second layer comprising hydrophilic fibers, are equally applicable to the first layer in a topsheet comprising a first and a second layers.

Apertures

The topsheet in the present disclosure may comprise a plurality of apertures. In nature, a nonwoven has pores between fibers. Apertures in the disclosures herein have a size distinctively bigger than such pores, and intend not to include such pores. To ensure material stability, the smallest edge-to-edge distance between the majority of the apertures regardless of their particular shape and width is at least 0.5 mm, or at least 1.5 mm or 2.0 mm. This distance is measured on the first surface of the topsheet.

The apertures may vary in shape. For example, the shape of the apertures as seen from the first surface of the first layer may be circular, elliptic, rectangular, or polygonal. In some configurations, the apertures have a circular shape, an elliptic shape, or a polygonal shape.

The tridimensional shape of the apertures may be cylindrical (e.g., with a circular or elliptic base), prismatic (e.g. with a polygonal base) or truncated cone or pyramidal.

Referring to FIGS. 3A-5, each of the apertures 5 may have a side wall 6. Referring to FIG. 3A, the side wall 6 may extend outwardly, away from non-apertured area of the second surface of the topsheet. The side walls of the apertures may form funnels or channels. The side wall 6 may not extend outwardly as shown in FIG. 3B.

The apertures may be tapered and take a conical shape such that the diameter of the aperture is larger at a part of the aperture proximate to the first surface of the nonwoven than the diameter of the aperture at the bottom edge of the aperture.

Such tapered configuration helps to reduce the risk of rewet, i.e. of body fluids passing back from components underneath the topsheet (such as the absorbent core) into and through the topsheet. For apertured hydrophobic topsheets, rewet occurs predominantly through the apertures. The tapered shape of the apertures can help to reduce rewet, as the diameter of the aperture towards the absorbent core is smaller than the diameter of the aperture in the first layer.

The plurality of apertures may also vary in width.

The size of apertures may be determined to achieve the desired fluid and/or air penetration performance and other performances expected by wearers. If the apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased.

Each of the plurality of apertures may have a size ranging from $0.2 \text{ mm}^2$ to $1.5 \text{ mm}^2$, from $0.2 \text{ mm}^2$ to $1.0 \text{ mm}^2$, or from $0.25 \text{ mm}^2$ to $0.5 \text{ mm}^2$, and/or a diameter ranging from 0.3 mm to 1.5 mm, or from 0.3 mm to 1 mm, or from 0.4 mm to 0.8 mm. The plurality of apertures may have regular shapes selected from the group consisting of circle, oval, triangle, square, rectangle, parallelogram, trapezoid, polygon, hourglass, star, and any combinations thereof.

The nonwoven constituting the topsheet have at least 2.5% of open area, or at least 3% of open area, or at least 5% of open area for the fast fluid acquisition speed purposes. The nonwoven may have an open area no greater than about 30%, or no greater than 25%, or no greater than 20% for mitigating or preventing rewet purposes.

FIGS. 6 and 7 are schematic top views of exemplary nonwoven 30 constituting topsheet 24. Referring to FIG. 7, in some embodiments, the nonwoven 30 may comprises clustered apertures. The term "clustered apertures" herein intends to mean an aperture pattern wherein at least one aperture having at least three adjacent apertures wherein the one aperture and each of the at least three adjacent apertures has an edge-to-edge space S (shortest space between an edge of one aperture to an edge of an adjacent aperture) no greater than about 2.5 mm, preferably no greater than about 2 mm.

The aperture pattern in the topsheet may coordinate with graphics, indicia, printing, inks, color, and/or patterned adhesives, for example, located in the topsheet or in another component of an absorbent article when it is used as a component of an absorbent article.

Fluid Management Layer

One function of a fluid management layer is to quickly acquire liquids or other bodily exudates from a topsheet and transfer and distribute them to the absorbent core in an efficient manner.

The fluid management layer in the absorbent article of the present disclosure is disposed directly or indirectly on top of an absorbent core. It comprises a spacer woven fabric comprising a top face, a bottom face, and a plurality of yarns interconnecting the top and bottom faces, wherein the top and bottom faces are spaced apart from each other.

The top face and the bottom face of the spacer woven fabric may have the same configuration, or have different configurations in order to direct the fluid flow speed.

The spacer woven fabric may comprise thermoplastic fibers including polyesters, polyamides, polyolefins such as polyethylenes and polypropylenes, or any mixtures thereof.

The spacer woven fabric may further comprise absorbent fibers. Optional absorbent fibers can provide absorption of liquid insults from the wearer-facing surface or topsheet. Any suitable absorbent material may be utilized for the absorbent fibers. Some examples of absorbent materials include cotton, pulp, rayon or regenerated cellulose or combinations thereof. The spacer woven fabric may not comprise absorbent materials such as absorbent fibers and superabsorbent polymers. The top face and the bottom face of the spacer woven fabric may be made from the same fibers, or made from different fibers. At least one of the top face and the bottom face comprises polyethylene terephthalate ("PET") fibers.

The spacer woven fabric may also contain surfactant to facilitate fluid penetration in order to be drained quickly and not hold fluid unnecessarily long, thus maintaining free volume capacity for the next gush of fluid.

The spacer woven fabric may have a basis weight from about 150 gsm to 350 gsm, or from about 200 gsm to about 300 gsm, or from about 150 gsm to about 250 gsm.

The spacer woven fabric may have a caliper in the range of from about 1.0 mm to about 2.5 mm as measured according to Spacer Woven Fabric Dimension Test. If the caliper is too small, it may negatively impact fluid acquisition speed. If the caliper is too high, an absorbent article comprising the spacer woven fabric may not fit well to the wearer's body.

Each of the yarns interconnecting the first and second faces in the spacer woven fabric disclosed herein may comprise about 2 filaments to about 60 filaments. Multiple filaments constituting yarns create inter-filament microchannels which can enhance fluid wicking and faster fluid transport. Filaments constituting yarns may have a fineness of 1.5-10 dtex, or 3-8 dtex, or 2-5 dtex. If the filaments are too thin it may negatively impact on resilience of the spacer woven fabric and fluid acquisition speed. If the filaments are too thick, the material may be stiff with a higher rewet.

The top and bottom faces of the spacer woven fabric have may openings in order to ensure a rapid inflow and effective distribution of body fluid. The bottom face of the spacer woven fabric may have a more closer structure with relatively small openings than the top face. In one embodiment, the top face of the spacer woven fabric comprises openings, the openings have an opening area no less than about 0.2 $mm^2$ as measured according to Spacer Woven Fabric Dimension Test.

The yarn may form channels for fluid flow between the first and second faces in order to efficiently distribute and transfer the fluid to the absorbent core. In addition, due to the large void space between the first and second faces in the spacer woven fabric, the spacer woven fabric can accommodate and temporarily hold a relatively large fluid volume. Thus, body fluid discharged can be effectively received into the spacer woven fabric, and can flow it to parts of the absorbent core comprising an absorbent material where the body fluid is absorbed. Especially when the absorbent core comprises superabsorbent polymers which have a high absorption capacity but a relatively slow absorption speed, the fluid management layer disposed above the absorbent core enables the absorbent core to fully utilize its high absorption capacity by temporarily holding fluid volume.

The spacer woven fabric is orientated in the absorbent article in such a way that the top face of the spacer woven fabric is facing the direction of the topsheet and the bottom face of the spacer woven fabric is facing the direction of the backsheet.

In addition, due to the unique spacer woven fabric structure, the absorbent article of the present invention can have a high compression resistance without significant increase in a basis weight or volume of an absorbent article.

Absorbent Core

The absorbent core comprises an absorbent material.

The absorbent material in the absorbent core can be any liquid-absorbent material commonly used in disposable absorbent articles such as comminuted wood pulp, which is generally referred to as airfelt or fluff. Examples of other suitable liquid-absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (herein abbreviated as "SAP"), absorbent gelling materials, or any other known absorbent material or combinations of materials. The term "superabsorbent polymer" refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it did not exclude that other forms of SAP may be used such as a superabsorbent polymer foam, for example.

Backsheet

Any conventional liquid impervious backsheet materials commonly used for absorbent articles may be used as a backsheet. In some configurations, the backsheet may be impervious to malodorous gases generated by absorbed bodily discharges, so that the malodors do not escape. The backsheet may or may not be breathable.

Measurement

1. Contact Angle Test

All measurements are performed in a laboratory maintained at 23° C.±2 C.° and 50%±2% relative humidity.

A rectangular specimen measuring 10 mm×50 mm is cut from a raw material nonwoven or a topsheet of a disposable absorbent article with taking care not to touch the surface of the specimen or not to disturb the structure of the material. The specimen has a length of 5 cm and is aligned with a longitudinal centerline of the absorbent article if it is cut from an absorbent article. The specimen is handled gently by the edges using forceps and mounted flat on a sample stage of an optical microscope such as Keyence VHX 5000 or equivalent. An appropriate light source, magnification and camera position are adjusted to make a cross-section view of the specimen shown clearly.

Figure 8A:
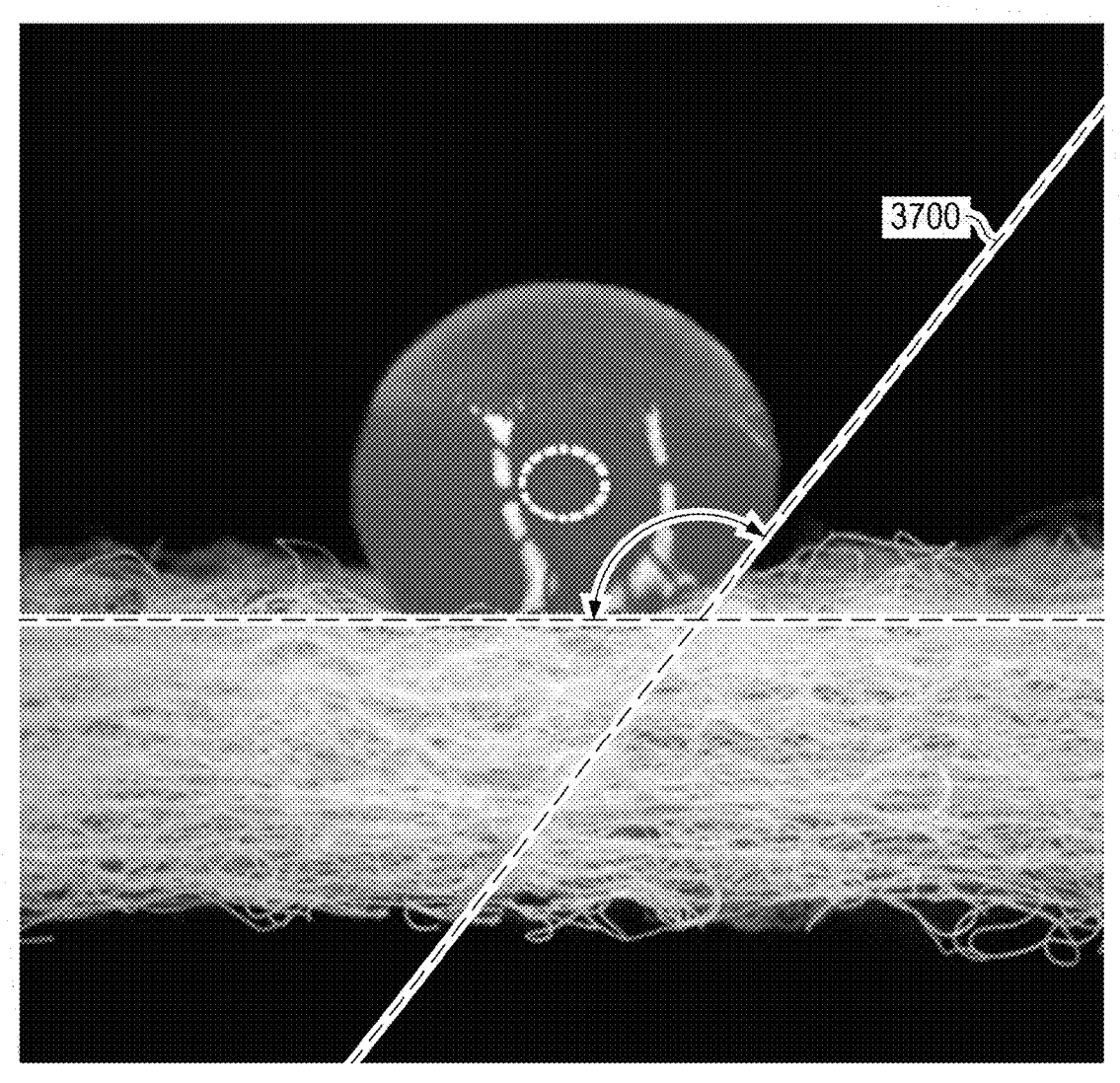
FIG. 8A is an image of an exemplary water droplet having a contact angle greater than 90 degrees according to Contact Angle Test method disclosed herein.
Figure 8B:
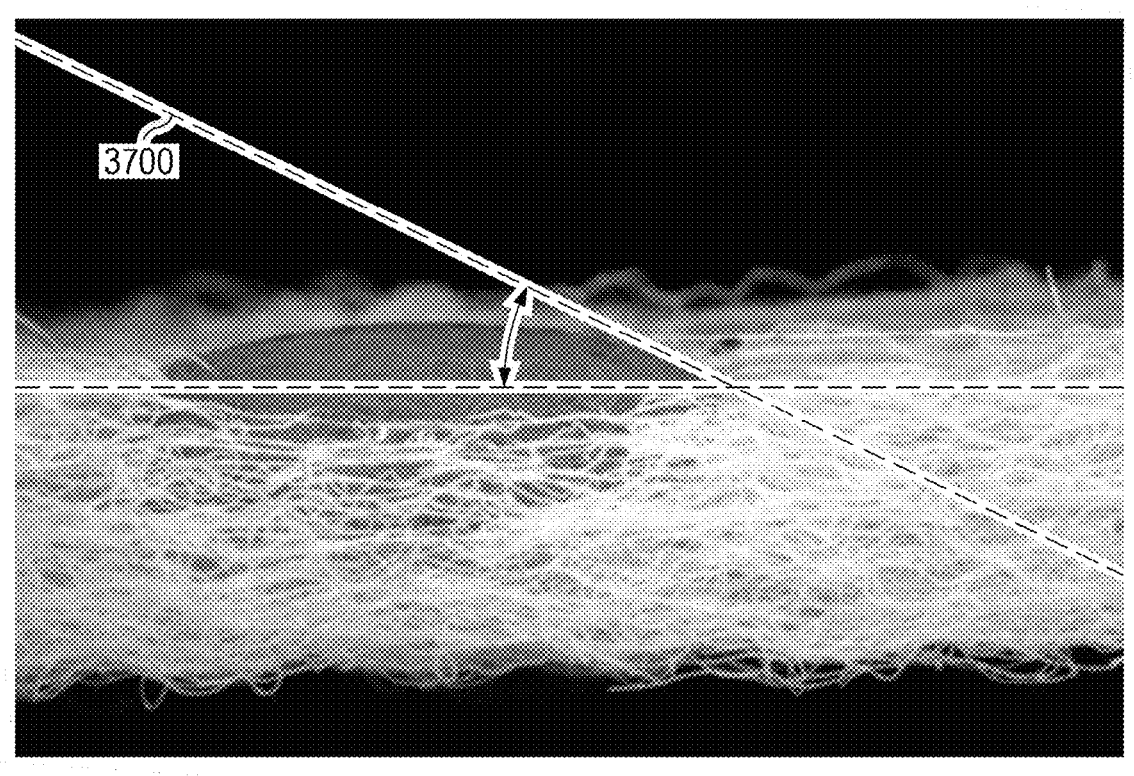
FIG. 8B is an image of an exemplary water droplet having a contact angle no greater than 90 degrees according to Contact Angle Test method disclosed herein.
Figure 9A:
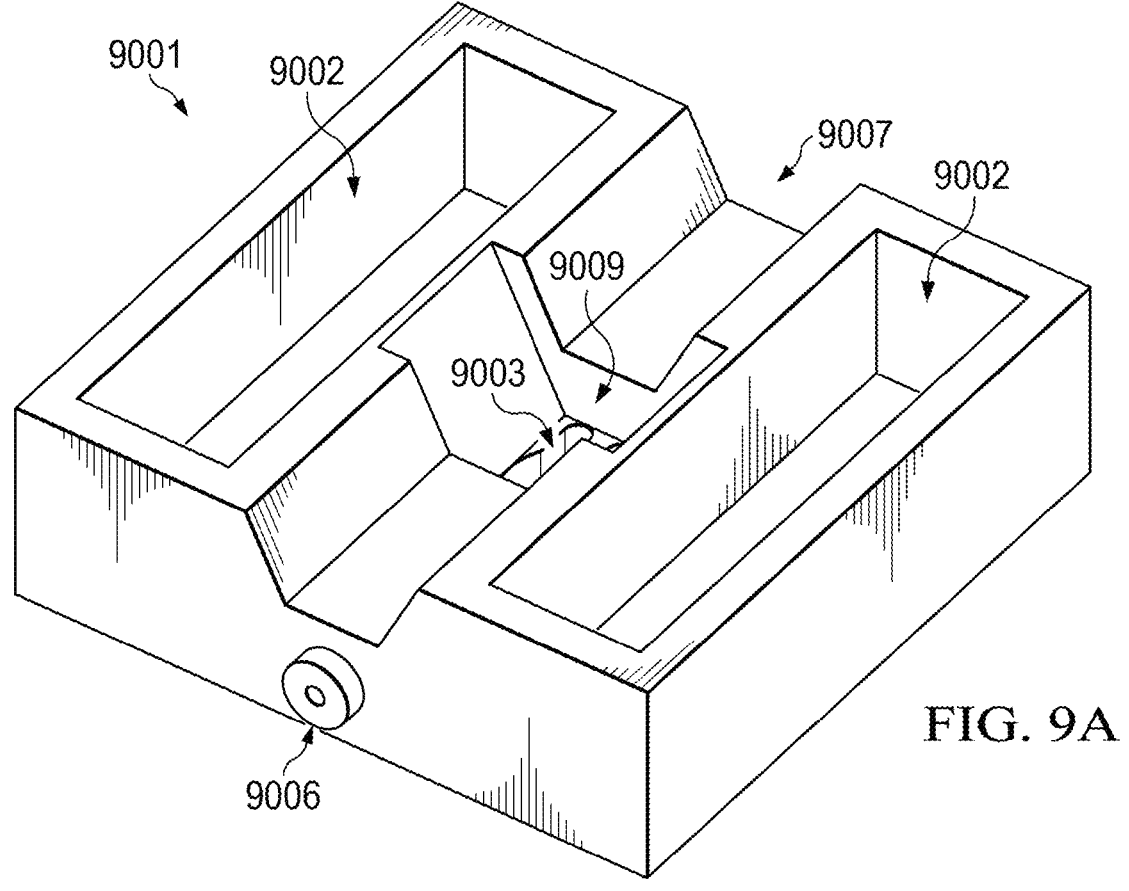
FIG. 9A is a perspective view of a strikethrough plate for acquisition time measurement.
Figure 9B:
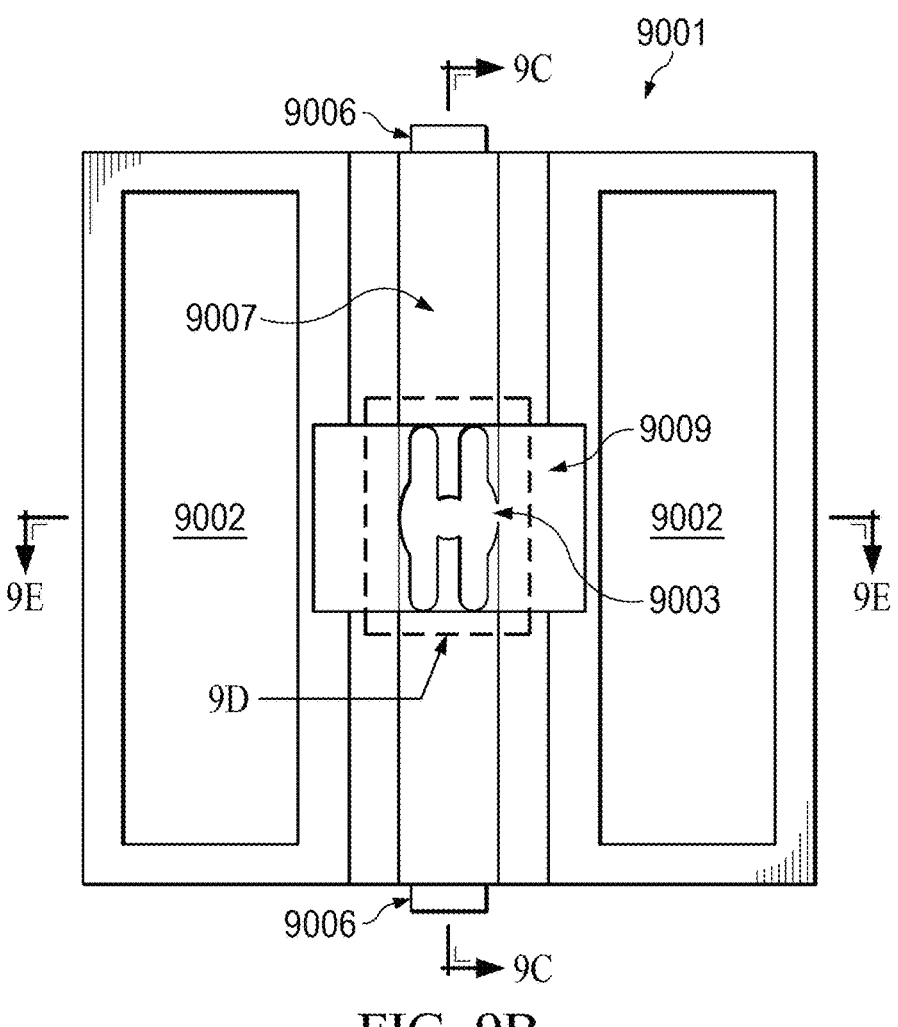
FIG. 9B is a plan view of the strikethrough plate of FIG. 9A.
Figure 9C:
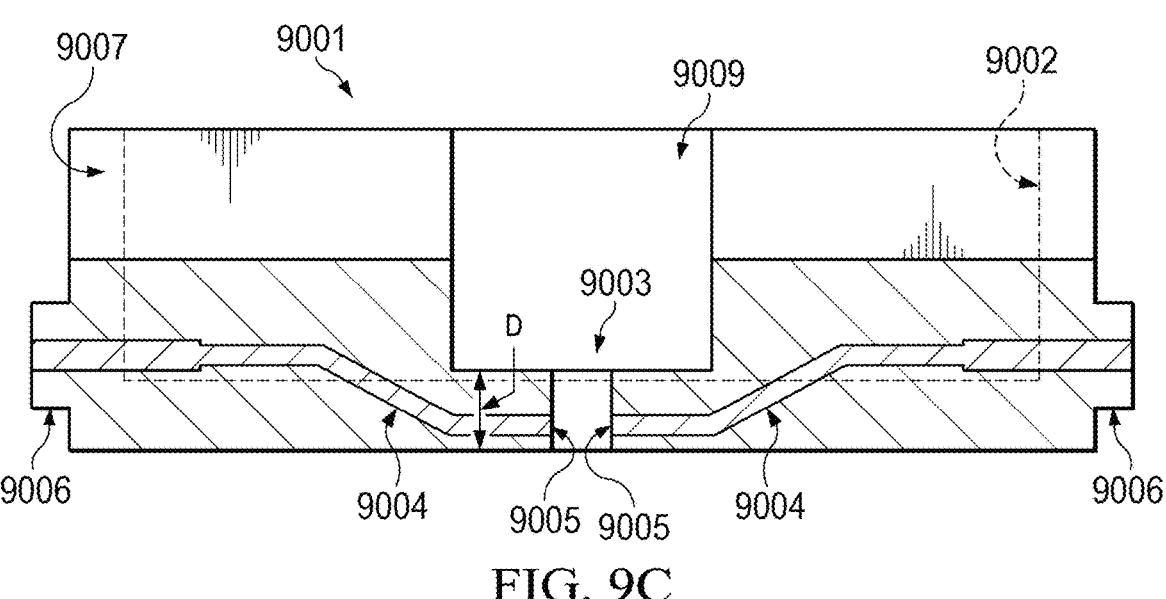
FIG. 9C is a plan view of a 9C-9C direction cross section of the strikethrough plate of FIG. 9B.
Figures 9D, 9E:
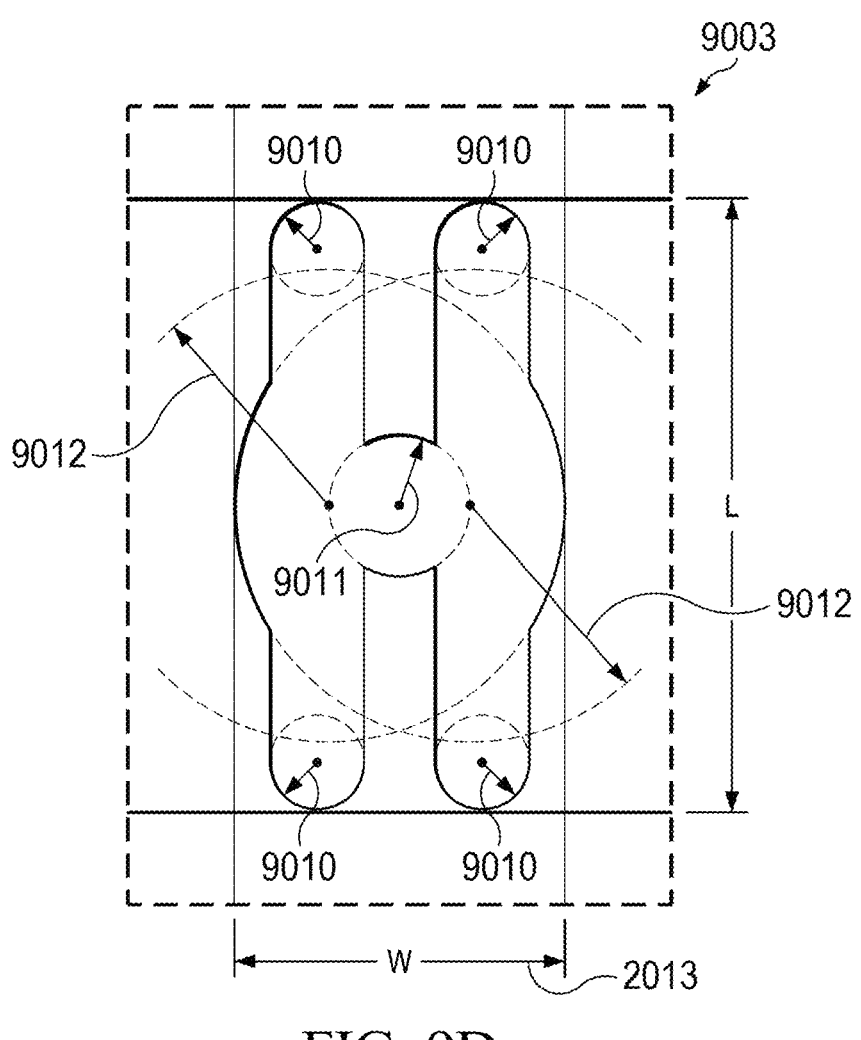
FIG. 9D is a plan view of part pf the strikethrough plate of FIG. 9B.
FIG. 9E is a plan view of a 9E-9E direction cross section of the strikethrough plate of FIG. 9B.

One water droplet with a volume of approximately 0.05 ml is gently deposited onto the specimen from in a close distance no longer than 1 cm above tested surface of the specimen. Keyence VHX 5000 or equivalent instrument is used to obtain a high-resolution image of a water droplet on the tested surface of the nonwoven specimen. These steps are repeated to obtain multiple water droplet images. Suitable water droplet images where each water droplet is oriented such that the projection of the water droplet extending from the nonwoven surface is approximately maximized. The contact angle between the water droplet and the specimen is measured to the nearest 0.1 degree directly from the image taken as is shown via lines 3700 in FIG. 8A and FIG. 8B. FIG. 8A is an exemplary image of a water droplet having a contact angle greater than 90°. FIG. 8B is an exemplary image of a water droplet having a contact angle less than 90°.

The measurement is performed on an area of a test nonwoven where no aperture exists. Five separate droplets are imaged from which ten contact angles, i.e., one on each side of each imaged droplet are measured. The arithmetic mean of the ten contact angle values is calculated to the nearest 0.1 degree, and reported as the surface contact angle.

2. Artificial Menstrual Fluid ("AMF") Preparation

AMF is composed of a mixture of defibrinated sheep blood, a phosphate buffered saline solution and a mucous component, and has a viscosity between 7.15 cSt to 8.65 cSt at 23±1° C.

Viscosity on the AMF is performed using a low viscosity rotary viscometer such as Cannon LV-2020 Rotary Viscometer with UL adapter (Cannon Instrument Co., State College, US) or equivalent. The appropriate size spindle for the viscosity range is selected, and instrument is operated and calibrated as per the manufacturer. Measurements are taken at 23±1 C.° and at 60 rpm. Results are reported to the nearest 0.01 cSt.

Defibrinated Sheep Blood

Defibrinated sheep blood with a packed cell volume of 38% or greater collected under sterile conditions (available from Cleveland Scientific, Inc., Bath, OH, US) or equivalent is used.

Phosphate Buffered Saline Solution

The phosphate buffered saline solution consists of two individually prepared solutions (Solution A and Solution B). To prepare IL of Solution A, add 1.38±0.005 g of sodium phosphate monobasic monohydrate and 8.50±0.005 g of sodium chloride to a 1000 mL volumetric flask and add distilled water to volume. Mix thoroughly. To prepare IL of Solution B, add 1.42±0.005 g of sodium phosphate dibasic anhydrous and 8.50±0.005 g of sodium chloride to a 1000 mL volumetric flask and add distilled water to volume. Mix thoroughly. Add 450±10 mL of Solution B to a 1000 ml beaker and stir at low speed on a stir plate. Insert a calibrated pH probe (accurate to 0.1) into the beaker of Solution B and add enough Solution A, while stirring, to bring the pH to 7.2±0.1.

Mucous Component

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. A successful range of gastric mucin is usually between 38 to 50 grams. To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range, then remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the mucous component and add it to a 1200 mL beaker. Add an equal volume of sheep blood to the beaker and mix thoroughly. Using the viscosity method previously described, ensure the viscosity of the AMF is between 7.15-8.65 cSt. If not, the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

3. Rewet Test

Rewet is measured for an absorbent article loaded with Artificial Menstrual Fluid ("AMF") as described herein.

The fluid amounts left on a topsheet, i.e., rewet, under pressure of 0.1 psi and 0.5 psi are measured after 3.0 ml, 6.0 ml, 9.0 ml and 12 ml AMF are dispensed. All measurements are performed in a laboratory maintained at 23° C.±2 C.° and 50%+2% relative humidity.

Test products are removed from all packaging using care not to press down or pull on the products while handling. No attempt is made to smooth out wrinkles. The test products are conditioned at 23° C.±2 C.° and 50%±2% relative humidity for at least 2 hours prior to testing.

Place the test product onto a flat, horizontal surface with the body side facing up and load a strikethrough plate on the center of the test product to apply a pressure of 0.25 psi on the test product.

Referring to FIGS. 9A-9E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 9004 6 mm apart. The lateral sides of the reservoir bow outward at a radius 9012 of 14 mm bounded by the overall width, W, of 15 mm. Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm²) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003.

Use a pipette to carefully dispense 3.0 ml of AMF through the open hole of the strikethrough plate onto the center of the test articles within 2 seconds. Once the gush fluid is acquired, remove the plate and start the timer for 3 minutes. After removing the plate, quicky acquire an image of a topsheet of the test product using a color scanner HP Scanjet G4010 or equivalent, and clean the scanner surface after each scan. The image will be analyzed to measure the stain size and redness on a topsheet under Stain Size and Redness Test described below. At the end of 3 minutes, place 5 pieces of filter paper (a typical lab filter paper, for example, Ahlstrom #632 12.7 cm×12.7 cm filter papers) that are pre-weighed (termed as "dry weight") are placed on top of an approximate center of an area stained with the fluid. Apply the required mass to generate 0.1 psi pressure on the top of the test product, and keep it under pressure for 5 seconds. Weigh the filter papers again (termed as "wet weight"). The difference between the wet weight and dry weight of the filter paper is the light pressure rewet at the added amount of fluid.

Repeat the step above till total 12.0 ml of fluid is dispensed on the test product. Report the rewet values to the nearest 0.001 gram for the gush level of 3.0 ml, 6.0 ml, 9.0 ml and 12.0 ml. In like fashion, a total of three replicate samples are tested for each test product to be evaluated. The arithmetic mean of the replicates is calculated to the nearest 0.001 gram, and reported as the rewet at 0.1 psi.

The same rewet test is conducted by applying the required mass to generate 0.5 psi pressure on the top of the test product to obtain rewet at 0.5 psi.

Total rewet is calculated according to the equation below.
Total rewet (g)=rewet at 0.1 psi+rewet at 0.5 psi 4. Stain Size and Redness Test The size and redness of a stain visible on a topsheet of an absorbent article due to the fluid left on the topsheet are measured on topsheet images of test products acquired in Rewet Test above for the gush level of 3.0 ml, 6.0 ml, 9.0 ml and 12.0 ml.

4.1 Stain Size Test

Image analysis is performed using image analysis program such as Image J software (version 1.52p or above, National Institute of Health, USA) or equivalent. The image needs to be distance calibrated with an image of a ruler to determine the image resolution.

Open a topsheet image in Image J. Set the scale according to the image resolution. Crop the image in the center area to make a minimum bounding rectangular selection around the total stain region visible across multiple pad layers. Convert the image type to 8 bit. Apply a Gaussian blur filter to smooth the image by a Gaussian function with a Sigma (radius) of 2. The filtered 8-bit grayscale image is then converted to a binary image using the "Minimum" thresholding method to find the boundary of the stain region on the topsheet (as a result of fluid left on the topsheet) against the lighter-colored stain region from the subsequent layers.

The area of the selected stain region on the topsheet is obtained and recorded as topsheet stain size to the nearest 0.01 cm². This entire procedure is repeated on three substantially similar replicate articles. The average of the three individual recorded measurements for topsheet Stain Size to the nearest 0.01 cm² the topsheet Stain Size 4.2 Stain Redness Test Stain redness on topsheet is indicated as the Stain Redness Saturation Integral which is calculated based on the HSB color model using a color representation by three parameters: Hue (0°-360°), saturation (0-100) and brightness (0-100). A suitable hue range, for example, the combination of 240°-360° and 0°-45° is selected for a topsheet image to represent the total red stain on a topsheet of the test product. For the selected red stain area based on the hue range, saturation histogram is obtained, and pixels corresponding to each color saturation level in the selected saturation range of 35 to 100 are counted. The Stain Redness Saturation Integral is calculated using the equation below:

$$\text{Stain Redness Saturation Integral} = \sum_{i=35}^{100} i \times P_i$$

where $P_i$ is defined as the count of pixels at the color saturation level i.

5. Acquisition Time Test

Acquisition time is measured for an absorbent article loaded with AMF as described herein, using a strikethrough plate and an electronic circuit interval timer. The time required for the absorbent article to acquire a dose of AMF is recorded. All measurements are performed in a laboratory maintained at 23° C.±2 C.° and 50%±2% relative humidity.

Referring to FIGS. 9A-9E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 9004 6 mm apart. The lateral sides of the reservoir bow outward at a radius 9012 of 14 mm bounded by the overall width, W, of 15 mm. Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm²) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003. A circuit interval timer (not shown in the drawings) is plugged into the jacks 9006, and monitors the impedance between the two electrodes 9004, and measures the time from introduction of the AMF into reservoir 9003 until the AMF drains from the reservoir. The timer has a resolution of 0.01 sec.

Test products are removed from all packaging using care not to press down or pull on the products while handling. No attempt is made to smooth out wrinkles. The test samples are conditioned at 23° C.±2 C.° and 50%±2% relative humidity for at least 2 hours prior to testing.

The required mass of the strikethrough plate must be calculated for the specific dimensions of the test article such that a confining pressure of 1.72 kPa is applied. Determine the longitudinal and lateral midpoint of the article's absorbent core. Measure and record the lateral width of the core to the nearest 0.1 cm. The required mass of the strikethrough plate is calculated as the core width multiplied by strikethrough plate length (10.2 cm) multiplied by 17.6 gf/cm² and recorded to the nearest 0.1 g. Add lead shot to the plate to achieve the calculated mass.

Connect the electronic circuit interval timer to the strike-through plate 9001 and zero the timer. Place the test product onto a flat, horizontal surface with the body side facing up. Gently place the strikethrough plate 9001 onto the center of the test product ensuring that the "H" shaped reservoir 9003 is centered over the test area.

Using a mechanical pipette, accurately pipette 3.00 mL±0.05 mL of AMF into the test fluid reservoir 9003. The fluid is dispensed, without splashing, along the molded lip of the bottom of the reservoir 9003 within a period of 3 seconds or less. After the fluid has been acquired, record the acqui-sition time to the nearest 0.01 second. Thoroughly clean the electrodes 9004 before each test.

In like fashion, a total of three replicate samples are tested for each test product to be evaluated. The arithmetic mean of the replicates is calculated to the nearest 0.01 sec, and reported as the Acquisition Time (sec).

6. Spacer Woven Fabric Dimension Test

Spacer woven fabric dimension is measured using Scan-ning Electron Microscope (SEM) images. SEM images are obtained and analyzed as follows to determine the spacer woven fabric dimension.

(1) Specimen Preparation

When spacer woven fabric is available in a raw material form, a specimen with a size of 10 mm×5 mm is cut from the raw material. When spacer woven fabric is a component of a finished product, a specimen is removed from the layer of spacer woven fabric in the finished product using a razor blade to provide a specimen with a size of 10 mm×5 mm. A cryogenic spray (such as Sunto™ Freeze Spray, Sunto (HK) International, China) may be used to remove the specimen from other components of the finished product. Care should be taken to prevent stretching of the spacer woven fabric during the separation process. If necessary, a specimen may be removed from the finished product by submerging the components in tetrahydrofuran (THF) with 15 minute gentle stirring and 5 minute soaking.

(2) SEM Image Acquisition

Figure 10A:
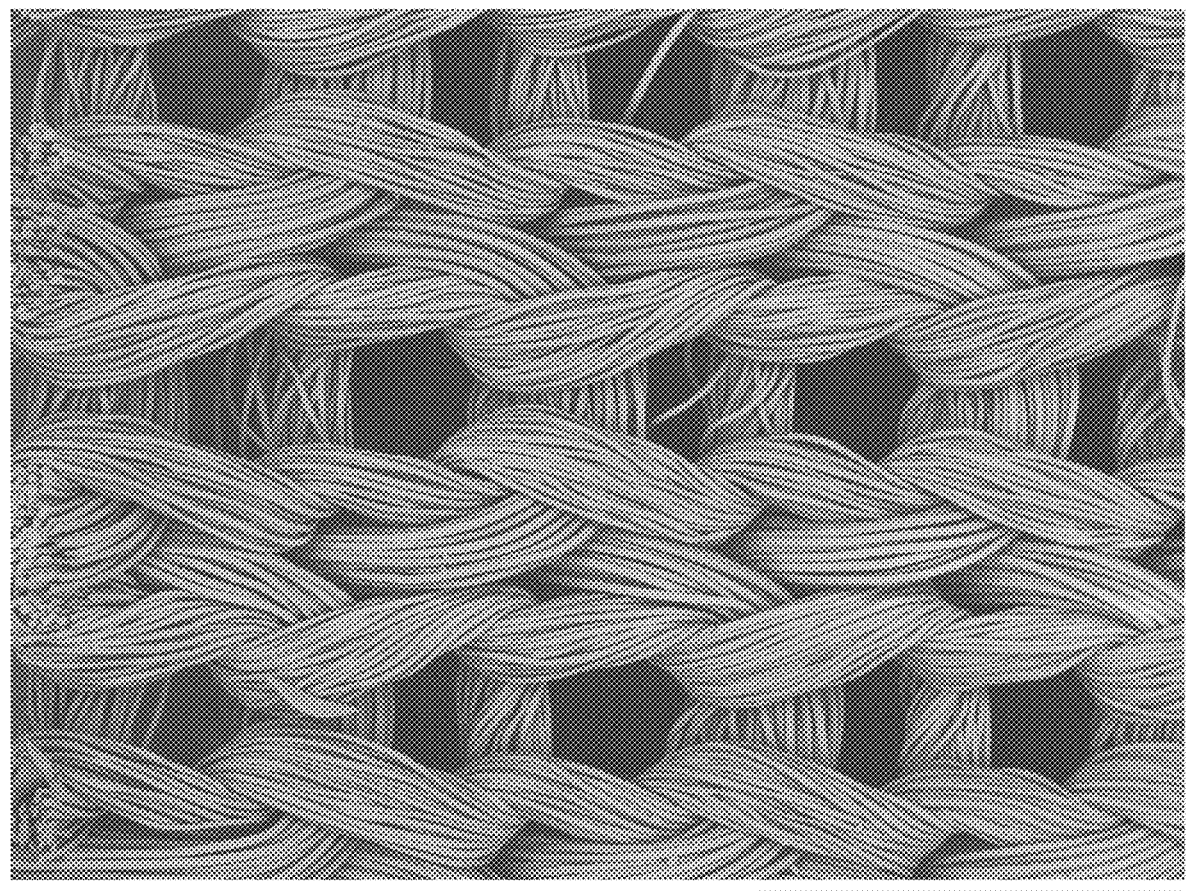
FIG. 10A is an SEM plan view image of an exemplary spacer woven fabric.

SEM images are obtained using a Scanning Electron Microscope (SEM), such as the Tabletop Microscope TM3000 (Hitachi, Japan), or equivalent. The specimen is mounted flat or vertically on a horizontal sample stage for a top view image such as FIG. 10A and a cross-section view image such as FIG. 11 respectively, with the second face of the spacer woven fabric attached to the carbon tape. Then the specimen is sputtered with platinum, to avoid electric charg-ing and improve overall conductivity, under the conditions of 15 mA current and 120 second coating time. The plati-num-coated specimen is subsequently transferred into the SEM specimen vacuum chamber for the imaging.

An appropriate magnification and working distance are chosen such that the top face 112 or cross-section structure is suitably enlarged for measurement. For cross-section imaging, the cross-sectional edge of the specimen is oriented such that it is substantially aligned to the horizontal direc-tion. The spacer woven fabric specimen is imaged at an acceleration voltage of 5 kV, and saved as an 8 bit jpeg images containing a linear distance scale for calibration.

(3) Image Analysis and Segmentation

Analyses are performed using image analysis program such as ImageJ software (version 1.52p or above, National Institutes of Health, USA) or equivalent. Open a specimen image in ImageJ. The SEM image needs to be distance calibrated with the corresponding scale bar and then cropped to remove the scale bar and image information labels so that only the specimen view is saved for subsequent image processing.

Convert the 8-bit grayscale image to a binary image (with "black" foreground pixels corresponding to the surface opening regions) using the "Minimum" thresholding method: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of openings and the lighter pixel peak of the specimen material. If the histogram contains either zero or one local maximum, the method cannot proceed further, and no output parameters are defined.

(4) Top Face Opening Area, Major Axis Length and Minor Axis Length

Figure 10B:
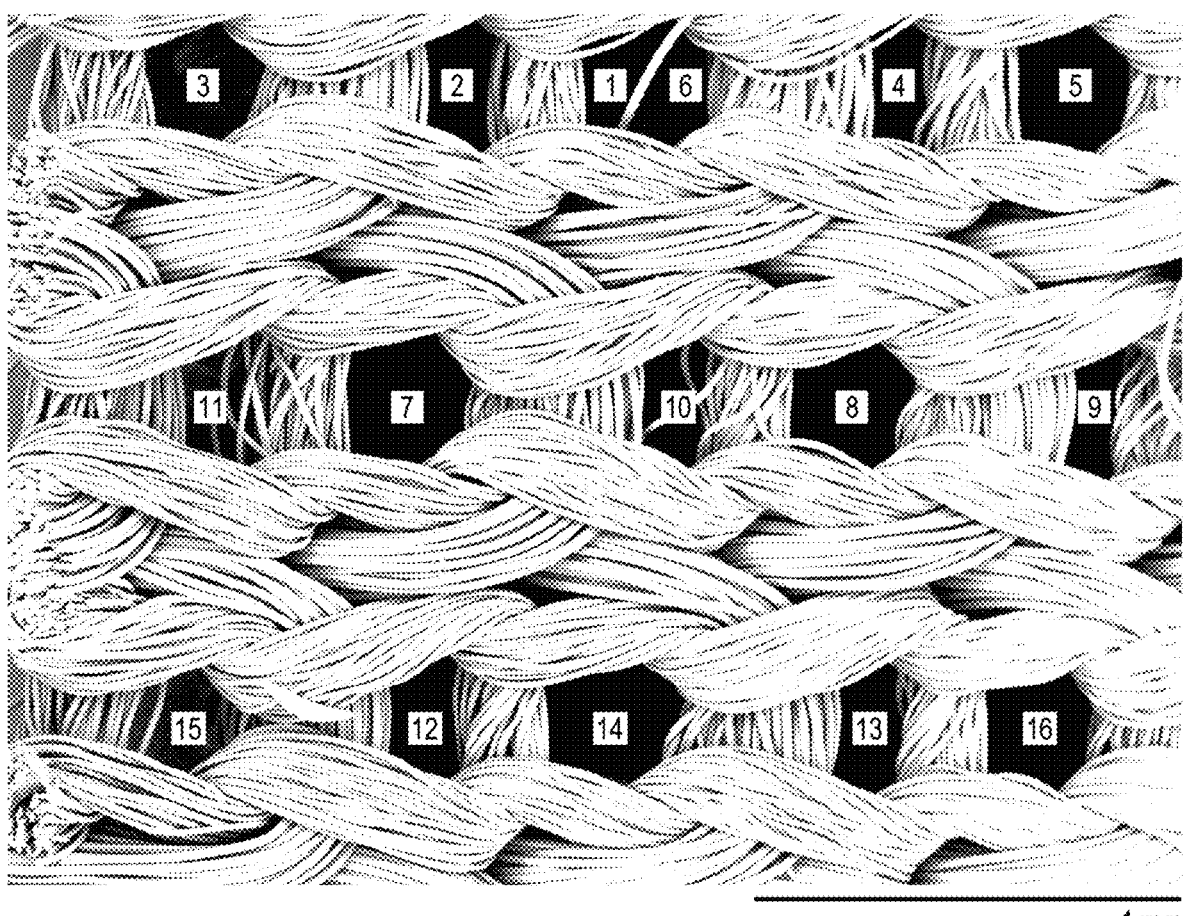
FIG. 10B is a processed image of FIG. 10A

Referring to FIG. 10B, set the scale for the binary image obtain in (3) according to the image resolution. Set the measurements to include the analysis of the top face opening area and shape descriptor (i.e., the major and minor axis lengths, after replacing an area selection with the best fit ellipse by keeping the same area, orientation and centroid as the original selection). Obtain the area, major axis length and minor axis length values of the top face openings, after tracing these openings by their outer edge and excluding the small openings with size below 0.020 mm² or incomplete openings at the edge of acquired image. At least ten open-ings need to be detected from the SEM image for measure-ments. Referring to FIG. 10B, in case one opening is split by a fiber (fibers) to sub-openings 1 and 6 in FIG. 10B, those sub-openings are disregarded. The area values of all these openings are analyzed to calculate the mean and standard deviation of the top face opening area to the nearest 0.001 mm², and the relative standard deviation (RSD, defined as the standard deviation divided by the mean and multiplied by 100) of the opening area to the nearest 0.1%. The major or minor axis length readings of all these openings are separately analyzed to calculate the corresponding mean and standard deviation values to the nearest 0.01 mm and RSD to the nearest 0.1%. Prepare and analyze a total of three substantially similar replicate specimens. Arithmetic means of the three replicates are calculated to the nearest 0.01 mm and reported as the top face opening area, major axis length, and minor axis length, respectively.

(5) Spacer Woven Fabric Thickness

Figure 11:
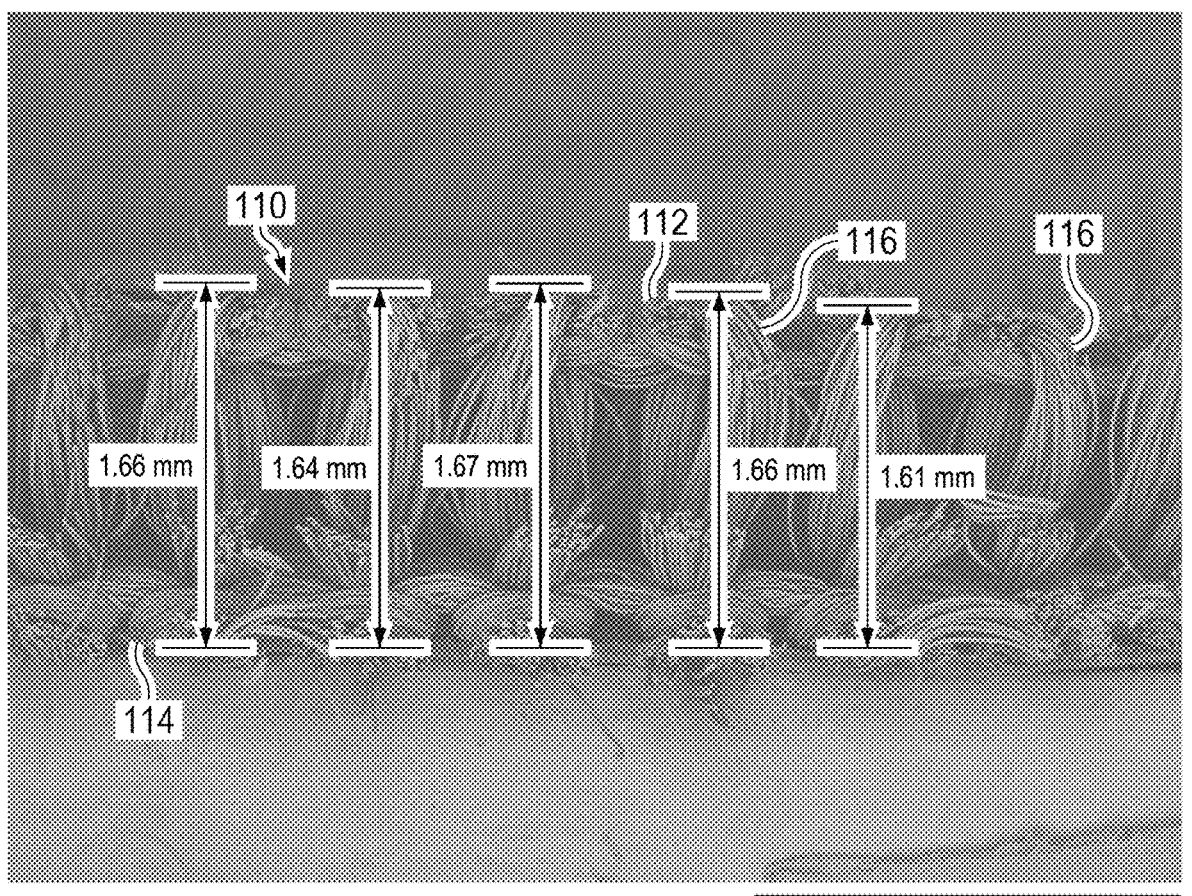
FIG. 11 is a cross section image of an exemplary spacer woven fabric.

Rotate the cross-section SEM image so that the top face 112 of the spacer woven fabric 110 is horizontally aligned. Referring to FIG. 11, the thickness of spacer woven fabric is measured at the position of the yarn 116 vertically connect-ing the top face 112 and the bottom face 114 of spacer woven fabric 110. Still referring to FIG. 11, the bottom edge of the bottom face 114 of spacer woven fabric 110 is defined by the top surface of the carbon tape layer attached on the sample holder. The top edge of the top face 112 of spacer woven fabric 110 is determined from the apex position of each yarn 116 vertically connecting two faces. The perpendicular distance between the apex position of a yarn 116 and the bottom edge of the bottom face 114 of spacer woven fabric 110 is measured for at least consecutive five piles of fila-ments. The arithmetic mean from these distance measurements is calculated to the nearest 0.01 mm. Prepare and analyze a total of three substantially similar replicate specimens. The arithmetic mean of the three replicates is calculated to the nearest 0.01 mm, and reported as the spacer woven fabric thickness.

EXAMPLES

Example 1. Nonwoven for Topsheet

Various nonwoven substrates having configurations as indicated in Table 1 were produced.

Nonwoven 1: 18 gsm spunbond nonwoven having apertures as shown in FIG. 6 was fabricated from 100% 2 denier hydrophobic PP fibers. Referring to FIG. 6, Nonwoven 1 has aperture 5a which has at least 3 adjacent apertures 5b, 5c and 5d where the edge-to-edge space S between aperture 5a and each of apertures 5b, 5c and 5d is 2.7 mm.

Nonwoven 2: 18 gsm carded air-through nonwoven was fabricated using 1.5 denier hydrophobic PE/PET sheath/core bicomponent fibers. Apertures having a pattern shown in FIG. 7 were formed on the nonwoven to fabricate Nonwoven 2. Referring to FIG. 7, Nonwoven 2 has aperture 5a which has at least 3 adjacent apertures 5b, 5c and 5d where each edge-to-edge space S between aperture 5a and each of type thermal treatment apparatus with a breathable conveyor belt. In the heat treatment, the overlaid web was placed on the breathable conveyor belt of the thermal treatment apparatus in such a way that the surface of the first fibrous web was in contact with the breathable conveyor belt. The 2 denier hydrophobic PE/PET bicomponent fibers have a fiber contact angle of 121.4°, and the 2 denier hydrophilic PE/PET bicomponent fibers have a fiber contact angle of 62.3° according to Contact Angle Test.

Nonwoven 4: Precursor Nonwoven 4 was produced using the same hydrophobic fibers and hydrophilic fibers as ones for Nonwoven 3 according to the same process as producing Nonwoven 3. Apertures having a pattern shown in FIG. 7 were formed on the precursor Nonwoven 4 to fabricate Nonwoven 4.

Nonwoven 5: 24 gsm carded air-through nonwoven was fabricated using 2 denier hydrophilic PE/PP bicomponent fibers.

Contact angles on a top surface and an opposite bottom surface in nonwovens were measured according to the Contact Angle Test, and indicated in Table 1 below. Contact angles of Nonwoven 4 were not tested given Nonwoven 4 is the same in nonwoven composition and structure as Nonwoven 3 except having apertures.

TABLE 1

|  | Nonwoven 1 | Nonwoven 2 | Nonwoven 3 | Nonwoven 4 | Nonwoven 5 |
|---|---|---|---|---|---|
| 1st layer | 18 gsm 2D hydrophobic PP | 18 gsm 1.5D hydrophobic PE/PET | 11 gsm 1.5D hydrophobic PE/PET | 11 gsm 1.5D hydrophobic PE/PET | 24 gsm 2D hydrophilic PE/PET |
| 2nd layer | — | — | 13 gsm 2D hydrophilic PE/PP | 13 gsm 2D hydrophilic PE/PP | — |
| aperture | FIG. 6 | FIG. 7 | No aperture | FIG. 7 | No aperture |
| First contact angle (°) | 133.6 | 107.5 | 92.4 | — | 0 |
| Second contact angle (°) | 131.4 | 122.5 | 63.1 | — | 0 | apertures 5b, 5c and 5d is 1 mm, 1 mm, and 2 mm, respectively. Aperture 5e has at least 3 adjacent apertures 5f, 5g and 5h where each edge-to-edge space S between aperture 5e and each of apertures 5f, 5g and 5h is about 1.5 mm, 1.5 mm, and 1 mm, respectively.

Nonwoven 3: The first fibrous web of 11 gsm was fabricated by laying down 1.5 denier hydrophobic sheath/core PE/PET bicomponent fibers constituting the first layer on a conveyer belt. The second fibrous web of 13 gsm was fabricated by laying down 2 denier hydrophilic PE/PP sheath/core bicomponent fibers constituting the second layer on a conveyer belt. The second fibrous web was overlaid on the first fibrous web, and the overlaid web was subjected to thermal treatment at the temperatures 130° C.-140° C. The thermal treatment was performed using a hot air through-

Example 2. Absorbent Articles

Sanitary napkins 1-8 as exemplary absorbent articles having topsheets made by nonwoven substrates in Example 1 and fluid management layer, absorbent core specified in table 2, and a common backsheet. Sanitary napkins 1-5 were fabricated using a common fluid management layer and absorbent core, and Sanitary napkins 6-8 were fabricated using a common fluid management layer and absorbent core.

An acquisition speed, and rewets at 0.1 psi/g and 0.5 psi/g of each of sanitary napkins 1-8 were tested according to Acquisition Speed Test and Rewet Test disclosed herein. Topsheet Stain Redness Saturation Integral was measured and calculated according to Stain Size and Redness Test. Table 2 below includes the measurement results.

TABLE 2

| Sanitary napkin | 1 | 2 | 3 | 4 | 5 | 6 | 7 | 8 |
|---|---|---|---|---|---|---|---|---|
| Topsheet | Nonwoven 1 | Nonwoven 2 | Nonwoven 3 | Nonwoven 4 | Nonwoven 5 | Nonwoven 1 | Nonwoven 2 | Nonwoven 3 |
| Fluid management layer | 290 gsm spacer woven fabric*[1] | 290 gsm spacer woven fabric*[1] | 290 gsm spacer woven fabric*[1] | 290 gsm spacer woven fabric*[1] | 290 gsm spacer woven fabric*[1] | Nonwoven laminate*[3] | Nonwoven laminate*[3] | Nonwoven laminate*[3] |

TABLE 2-continued

| Sanitary napkin | | 1 | 2 | 3 | 4 | 5 | 6 | 7 | 8 |
|---|---|---|---|---|---|---|---|---|---|
| Absorbent core | | 88 gsm SAPP*2 | 88 gsm SAPP*2 | 88 gsm SAPP*2 | 88 gsm SAPP*2 | 88 gsm SAPP*2 | 120 gsm airlaid core*4 | 120 gsm airlaid core*4 | 120 gsm airlaid core*4 |
| Acquisition time (sec) | 3 ml | 69.18 | 51.01 | 8.61 | 12.51 | 10.36 | 65.51 | 122.23 | 33.69 |
| | 6 ml | 25.72 | 30.58 | 13.50 | 16.89 | 17.87 | 144.90 | 136.89 | 83.77 |
| | 9 ml | 28.01 | 29.25 | 15.11 | 19.70 | 16.60 | 208.36 | 181.19 | 105.78 |
| | 12 ml | 29.01 | 29.37 | 14.08 | 17.07 | 16.87 | 247.32 | 224.51 | 122.89 |
| Total Rewet (g) | 3 ml | 0.00 | 0.03 | 0.25 | 0.03 | 0.18 | 0.00 | 0.03 | 0.11 |
| | 6 ml | 0.11 | 0.30 | 1.28 | 0.81 | 1.32 | 0.11 | 0.30 | 0.36 |
| | 9 ml | 0.37 | 0.96 | 2.12 | 1.56 | 1.97 | 0.37 | 0.96 | 0.90 |
| | 12 ml | 0.76 | 1.69 | 2.37 | 2.16 | 2.36 | 0.76 | 1.69 | 1.68 |
| Topsheet Stain Redness Saturation Integral | 3 ml | 84.24 | 77.40 | 313.33 | 88.31 | 160.94 | 31.25 | 39.01 | 37.51 |
| | 6 ml | 126.63 | 151.72 | 664.66 | 286.13 | 552.73 | 62.46 | 31.77 | 95.63 |
| | 9 ml | 186.12 | 261.18 | 924.93 | 476.12 | 662.86 | 143.34 | 71.38 | 174.64 |
| | 12 ml | 255.11 | 486.21 | 1079.84 | 603.18 | 795.56 | 288.04 | 130.79 | 373.63 |

290 gsm spacer woven fabric*1: PET based textile material shown in FIGS. 10A and 11. The spacer woven fabric has a thickness of 1.65 mm, a top face opening area of 0.43 mm², a major axis length of 0.28 mm, and a minor axis length of 0.19 mm as measured according to Measurement 6. Spacer Woven Fabric Dimension Test.
88 gsm SAPP*2: absorbent core containing wet-laid pulp and 22 gsm SAP.
Nonwoven laminate*3: a top layer of 35 gsm carded air-through bonded nonwoven and a bottom layer of 40 gsm airlaid nonwoven.
120 gsm airlaid core*4: airlaid core containing pulp and 27 gsm SAP.

Sanitary napkins 1, 2, and 4 according to the present invention exhibit significantly faster acquisition time, and lower total rewet and topsheet Stain Redness Saturation Integral values compared to Sanitary napkins 3 and 5-8.

Sanitary napkin 1 and Sanitary napkin 6 differ in the fluid management layer and absorbent core, but have the same topsheet. Sanitary napkin 2 and Sanitary napkin 7 differ in the fluid management layer and absorbent core, but have the same topsheet. Sanitary napkins 1 and 2 exhibits significantly improvement in acquisition time and total rewet, and a significantly low topsheet Stain Redness Saturation Integral value compared to Sanitary napkins 6 and 7, respectively.

Sanitary napkin 1 having Nonwoven 1 as topsheet and Sanitary napkin 2 having Nonwoven 2 as topsheet exhibit relatively slow acquisition time at the first gush, i.e., first 3 ml, compared to Sanitary napkins 3-5. It may be 100% hydrophobic topsheets in Sanitary napkins 1 and 2 require longer time for first gush to get the topsheets wet. However both Sanitary napkins 1 and 2 exhibit fast acquisition time upon the second, third and fourth gushes, 6 ml, 9 ml and 12 ml, respectively.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a liquid permeable topsheet having a wearer facing surface and an opposite garment facing surface, wherein the topsheet comprises a nonwoven comprising a plurality of apertures;
a liquid impermeable backsheet;
an absorbent core disposed between the topsheet and the backsheet; and
a fluid management layer disposed between the topsheet and the absorbent core, the fluid management layer comprising a spacer woven fabric,
wherein the nonwoven comprises a first surface forming the wearer facing surface of the topsheet, and a second surface forming the garment facing surface of the topsheet, the first surface having a first contact angle of no lower than about 90 degrees as measured according to Contact Angle Test, and
wherein the spacer woven fabric comprises a top face, a bottom face, and a plurality of yarns interconnecting the top face and the bottom face, wherein the top and bottom faces are spaced apart from each other.

2. The absorbent article according to claim 1, wherein the nonwoven comprises a first layer comprising hydrophobic fibers.

3. The absorbent article according to claim 1, wherein the second surface of the nonwoven has a second contact angle of no lower than about 90 degrees as measured according to Contact Angle Test.

4. The absorbent article according to claim 1, wherein the second surface of the nonwoven has a second contact angle of lower than about 90 degrees as measured according to Contact Angle Test.

5. The absorbent article according to claim 4, wherein the nonwoven comprises a first layer and a second layer, wherein the second layer comprises hydrophilic fibers, wherein the second layer forms the garment facing surface of the topsheet.

6. The absorbent article according to claim 5, wherein the nonwoven has unitary structure.

7. The absorbent article according to claim 5, wherein the nonwoven is a laminate comprising the first and second layers.

8. The absorbent article according to claim 4, wherein the difference between the first contact angle and the second angle is at least about 10 degrees as measured according to Contact Angle Test.

9. The absorbent article according to claim 2, wherein the first layer has a basis weight no greater than 14 gsm.

10. The absorbent article according to claim 1, wherein the plurality of apertures comprise at least one aperture having at least three adjacent apertures that are spaced apart from by an edge-to-edge space no greater than about 2.5 mm.

11. The absorbent article according to claim 1, wherein each of the yarns comprise about 2-60 filaments.

12. The absorbent article according to claim 11, wherein the filaments have a fineness of about 1.5-10 dtcx.

13. The absorbent article according to claim 1, wherein the top face of the spacer woven fabric comprises openings, the openings have an opening area no less than about 0.2 $mm^2$ as measured according to Spacer Woven Fabric Dimension Test.

14. The absorbent article according to claim 1, wherein the spacer woven fabric has a caliper in the range of from about 1.0 mm to about 2.5 mm as measured according to Spacer Woven Fabric Dimension Test.

15. The absorbent article according to claim 1, wherein the absorbent core comprises superabsorbent polymers.

16. The absorbent article according to claim 1, wherein the absorbent article further comprises an additional fluid acquisition and/or distribution layer between the topsheet and the fluid management layer.

\* \* \* \* \*